(12) United States Patent
Brugger et al.

(10) Patent No.: US 11,305,059 B2
(45) Date of Patent: Apr. 19, 2022

(54) NEEDLE GUARD

(71) Applicant: NxStage Medical, Inc., Lawrence, MA (US)

(72) Inventors: James M. Brugger, Newburyport, MA (US); Christopher D. Pierson, Southborough, MA (US); Steven C. Alford, Marysville, WA (US)

(73) Assignee: NxStage Medical, Inc., Lawrence, MA (US)

(*) Notice: Subject to any disclaimer, the term of this patent is extended or adjusted under 35 U.S.C. 154(b) by 457 days.

(21) Appl. No.: 15/749,965

(22) PCT Filed: Aug. 5, 2016

(86) PCT No.: PCT/US2016/045885
§ 371 (c)(1),
(2) Date: Feb. 2, 2018

(87) PCT Pub. No.: WO2017/027413
PCT Pub. Date: Feb. 16, 2017

(65) Prior Publication Data
US 2018/0221592 A1 Aug. 9, 2018

Related U.S. Application Data

(60) Provisional application No. 62/202,792, filed on Aug. 8, 2015.

(51) Int. Cl.
*A61M 5/162* (2006.01)
*A61M 25/06* (2006.01)
(Continued)

(52) U.S. Cl.
CPC ....... *A61M 5/1626* (2013.01); *A61B 5/15074* (2013.01); *A61B 5/150641* (2013.01);
(Continued)

(58) Field of Classification Search
CPC .... A61B 15/150534; A61B 15/150633; A61B 15/150641; A61B 15/150885;
(Continued)

(56) References Cited

U.S. PATENT DOCUMENTS

| 5,112,311 A | 5/1992 | Utterberg et al. |
| 5,562,637 A | 10/1996 | Utterberg |

(Continued)

FOREIGN PATENT DOCUMENTS

| JP | 2000246748 A | 9/2000 |
| WO | 2014121119 A1 | 8/2014 |
| WO | 2016205869 A1 | 12/2016 |

OTHER PUBLICATIONS

Extended European Search Report that issued in the corresponding EP Application No. 16835717.6; dated Jan. 24, 2019.
(Continued)

*Primary Examiner* — Shefali D Patel
(74) *Attorney, Agent, or Firm* — Potomac Law Group, PLLC; George Dolina

(57) ABSTRACT

A needle set includes a needle guard and a winged needle. The needle guard has upper and lower jaws, each of the upper and lower jaws defining a channel and coming together at a hinge. The upper and lower jaws are separated by slots in sides of the needle guard, which slots divide the sides into upper and lower side walls, respectively. The winged needle can be inserted between the upper and lower jaws, with wings of the winged needle passing through the slots. The hinge has an opening and a tube connected to the winged needle passes through the opening.

18 Claims, 12 Drawing Sheets

(51) Int. Cl.
*A61B 5/15* (2006.01)
*A61M 5/50* (2006.01)
*A61M 5/32* (2006.01)

(52) U.S. Cl.
CPC ......... *A61B 5/150885* (2013.01); *A61M 5/50* (2013.01); *A61M 25/0631* (2013.01); *A61M 25/0637* (2013.01); *A61B 5/15003* (2013.01); *A61B 5/150259* (2013.01); *A61B 5/150389* (2013.01); *A61B 5/150503* (2013.01); *A61M 5/321* (2013.01); *A61M 5/3202* (2013.01); *A61M 5/3245* (2013.01); *A61M 5/3272* (2013.01); *A61M 2205/273* (2013.01)

(58) Field of Classification Search
CPC ........ A61B 5/150534; A61B 5/150633; A61B 5/150641; A61B 5/15074; A61B 5/150885; A61B 5/150916; A61M 5/1626; A61M 5/50; A61M 25/0618; A61M 25/0631; A61M 5/3202; A61M 5/321; A61M 5/322; A61M 5/3221; A61M 5/3243; A61M 5/3245; A61M 5/3271; A61M 5/3272; A61M 2005/3247; A61M 25/0612; A61M 25/0637; A61M 2205/27; A61M 2205/273
See application file for complete search history.

(56) References Cited

U.S. PATENT DOCUMENTS

| | | | |
|---|---|---|---|
| 5,704,924 A | | 1/1998 | Utterberg et al. |
| 5,772,638 A | * | 6/1998 | Utterberg .......... A61M 25/0631 604/171 |
| 5,921,969 A | * | 7/1999 | Vallelunga ........ A61M 25/0637 128/919 |
| 5,951,529 A | | 9/1999 | Utterberg |
| 7,175,610 B2 | * | 2/2007 | Mori ................. A61M 25/0631 604/171 |
| 7,591,804 B2 | * | 9/2009 | Utterberg .......... A61M 25/0631 604/162 |
| 9,039,675 B2 | | 5/2015 | Howell et al. |
| 2004/0102739 A1 | | 5/2004 | Nakajima |
| 2013/0088885 A1 | | 4/2013 | Wilson et al. |
| 2015/0359973 A1 | | 12/2015 | Onken et al. |

OTHER PUBLICATIONS

International Preliminary Report on Patentability International Application No. PCT/US2016/045885 dated Feb. 22, 2018.
International Search Report and Written Opinion for International Application No. PCT/US2016/045885 dated Jan. 17, 2017.
Extended European Search Report dated Oct. 21, 2020 for European Patent Application No. 20199209.6.

* cited by examiner

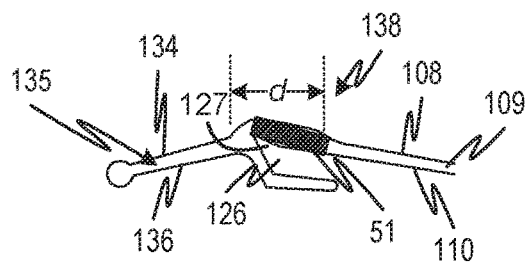
Fig. 8A
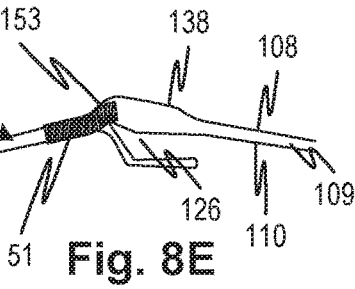
Fig. 8E
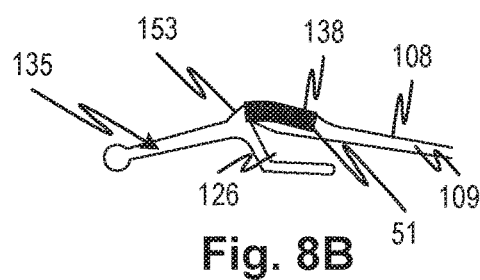
Fig. 8B
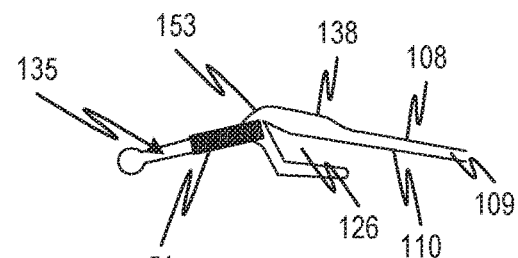
Fig. 8F
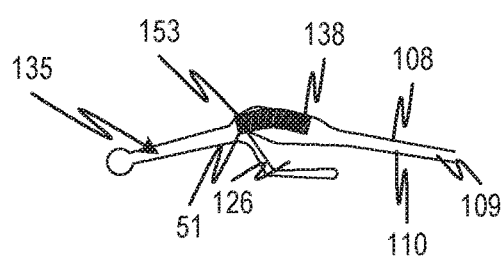
Fig. 8C
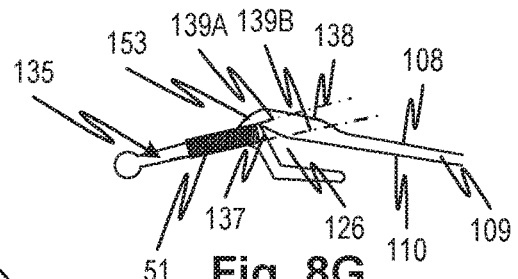
Fig. 8G
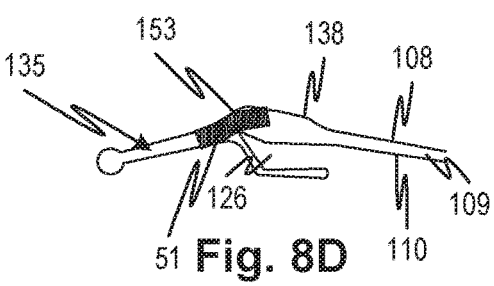
Fig. 8D
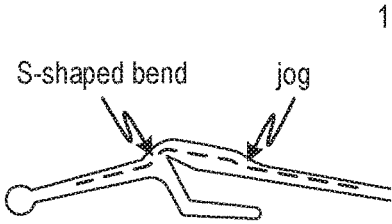
Fig. 8J
Fig. 8H

NEEDLE GUARD

CROSS-REFERENCE TO RELATED APPLICATIONS

This application is a U.S. national stage filing under 35 U.S.C. § 371 of International Application No. PCT/US2016/045885 filed Aug. 5, 2016, which claims priority to U.S. Provisional Application No. 62/202,792 filed on Aug. 8, 2015, all of which are hereby incorporated by reference in their entireties.

BACKGROUND

After a needle is used in medical care it is desirable to quickly cover the needle and render it incapable of subsequent punctures, especially for needles that are used in contact with blood. Utterberg et al. U.S. Pat. Nos. 5,112,311 and 5,562,637 disclose a sliding body or sheath carried on a tubular set such as a fistula set for hemodialysis, having a winged needle at the end. The sliding sheath or guard of the cited patent can be brought forward to enclose the needle as the needle is retracted from the patient, so that the needle is immediately secured against accidental needle punctures by the sliding needle guard. The wings of the needle, which are commonly used in conjunction with a variety of intravenous needles, slide within opposed slots of the needle protector of the cited patent, and are locked in place when the needle is fully withdrawn into the sliding sheath as described.

FIGS. 1A and 1B show a needle guard 1 according to the prior art. A needle guard 1 (also referred to as guard 1) has an upper jaw 4 and a lower jaw 6 joined at a hinge 7 formed in a monolithic structure defining a cavity 12 with slots on either side. The front slots 9 are defined by bottom edges 8 of the upper jaw side walls 13 and top edges 10 of the lower jaw side walls 14. The rear end of guard 1 is defined as the rounded wedge shape on the left side of FIG. 1A and the front end of guard 1 is defined as the end of upper jaw 4 shown on the right side of FIG. 1A. Side walls 13 and 14 have uniform thickness from the front end to the rear end. The front slots 9 define the cavity 12. As may be seen in the drawing, the front slots 9 (one on either side) are tapered such that the bottom edges 8 of upper jaw side wall 13 and top edges 10 of the lower jaw side wall 14 form an acute angle (indicated by the projecting lines 18 and 19). Further, the size of the slots is large, larger at the opening of cavity 12 than the thickness of the wings of a winged needle 90 shown in FIGS. 2A-2C, as indicated by the spacing between projecting lines 18 and 19. This facilitates easy capture of needle wings when the winged needle 90 is drawn into the guard 1, but it also makes it possible for tube 60 and the cannula 52 of the winged needle to pass somewhat sideways through the slot as shown in FIG. 2C. In a clinical environment where the process is repeated many times a day, there is a substantial risk of inattention or hasty withdrawals leading to a partially sideways pull on the needle tubing and consequent misalignment of the guard.

A rear slot 35 is defined between edges 34 and 36 that also taper as indicated by projections 30 and 32 that are aligned with the edges 34 and 36. The rear slot 35 receives wings of a winged needle as discussed below. The edges 34 and 36 form an acute angle as indicated by the projections 30 and 32 of the edges 34 and 36.

A resilient latch 26 is formed to catch the wings of a winged needle drawn into the rear slot 35. The latch 26 has a straight edge facing toward the upper jaw 4. A finger shield 2 extends forward from the front end 20 of the upper jaw 4 and curls up as shown in FIGS. 1A and 1B. The finger shield 2 has a uniform thickness through its entire length, except for a small drum shaped portion at its front end caused as a remnant of casting or molding. The finger shield 2 facilitates holding the guard 1 in position while the needle is drawn into it and further protects the user from the sharp needle point passing below the finger shield 2 when the tube 60 is pulled through needle guard 1. A front end 22 of the lower jaw 6 ends behind (i.e., extending less toward the front than) a front end 20 of the upper jaw 4 as highlighted by the angle formed between a line 17 that is perpendicular to the guard 1 major axis and a line 16 connecting the front end 22 of the lower jaw 6 that ends behind a front end 20 of the upper jaw 4.

A winged needle 90 includes a hub 49 which holds cannula 52, as illustrated in FIG. 2A. The hub has wings 53 each of which includes a thin wing portion 51 transitioning to thick wing portions 50 which are thicker than thin wing portions 51.

FIGS. 2A-2C illustrate a method of use of a prior art needle guard 1. When the cannula 52 is to be withdrawn from the patient, the guard 1 is held in place as the tube 60 is pulled back drawing the cannula 52 through the cavity 12 and the wings 53 into the slots 9 as shown in FIG. 2B. Thin wing portions 51 of wings 53 are supposed engage vertically with the front slot 9 while thick wing portions 50 are supposed remain horizontally outside the front slot 9 and provide horizontal stabilization. However, this is not always the case, given the large opening of the front slot 9.

If the tube 60 is pulled at an angle relative to the prior art needle guard 1, the cannula 52 can protrude through one of the slots 9 as shown in FIG. 2C thereby causing the needle to remain exposed and defeating the effect and purpose of the guard 1.

Even when the needle guard of the prior art is used properly, there is also a risk that a fingertip or other part of a user's or third party's body may be inadvertently pushed into or otherwise enter the tip creating a risk of an accidental puncture. The body part does not need to enter very far because the housed needle tip is not far from the front of the device.

SUMMARY

A needle guard reduces the risk of misalignment and concomitant protrusion of a needle due to imprecise use. In comparison to previous configurations, the inventive device may have narrowed slots that receive the wings of a winged needle. The slots may further be about as narrow as the wings are thick. The slots may further be narrower than the wings are thick. The slots may have parallel edges such that they have a uniform width over a substantial length thereof. The slots may have parallel edges such that they have a uniform width over a majority thereof.

In embodiments, the sides and/or rear end are reinforced to prevent the relative lateral movement of upper and lower jaws which may permit the needle to slip out the side through one of the slots once drawn into the guard. The resistance to this mode of movement may be further increased by forming the guard of high density polyethylene (HDPE). In embodiments, the HDPE has a flexural modulus of over 300 Mpa. In embodiments, the HDPE has a flexural modulus of over 1000 Mpa. In embodiments, the HDPE has a flexural modulus of at least 1200 Mpa.

In embodiments, the lower jaw extends beyond the upper jaw. This helps to protect against use with slightly longer needles due to manufacturing variability and incomplete retraction of the needle within the guard. It also facilitates holding and stabilizing the guard against the skin of the patient when the needle is retracted. The lower jaw may have a rounded forward edge or straight. The rounded edge may increase comfort while the straight forward edge may improve ease of manipulation.

In embodiments, a home slot that receives the needle wings in a locked position thereby retaining the needle within the guard, has a substantially constant width. In variants, the home slot is tilted further than prior art embodiments to push the needle up against the upper interior wall of the upper jaw.

In embodiments, ribs are molded into on the back end to facilitate use. The back end may be held rather than using an integral finger shield or guard to hold the shield or guard during the drawing of the needle into the guard.

In embodiments, a resilient latch by virtue of its shape and the use of HDPE provides a more distinct tactile feedback upon engagement of the wings.

Objects and advantages of embodiments of the disclosed subject matter will become apparent from the following description when considered in conjunction with the accompanying drawings. The foregoing summary does not comprehend all the embodiments or inventive aspects of the disclosed subject matter and serves merely to assist the reader.

BRIEF DESCRIPTION OF THE DRAWINGS

The accompanying drawings, which are incorporated herein and constitute part of this specification, illustrate exemplary embodiments of the disclosure, and, together with the general description given above and the detailed description given below, serve to explain the features of embodiments of the disclosed subject matter. The accompanying drawings have not necessarily been drawn to scale. Where applicable, some features may not be illustrated to assist in the description of underlying features.

FIGS. 8A-8H and 8J illustrate the progression of a needle hub wing through a needle guard with a bridge slot according to embodiments of the disclosed subject matter.

Embodiments will hereinafter be described in detail below with reference to the accompanying drawings, wherein like reference numerals represent like elements.

DETAILED DESCRIPTION OF THE EMBODIMENTS

Figure 1A:
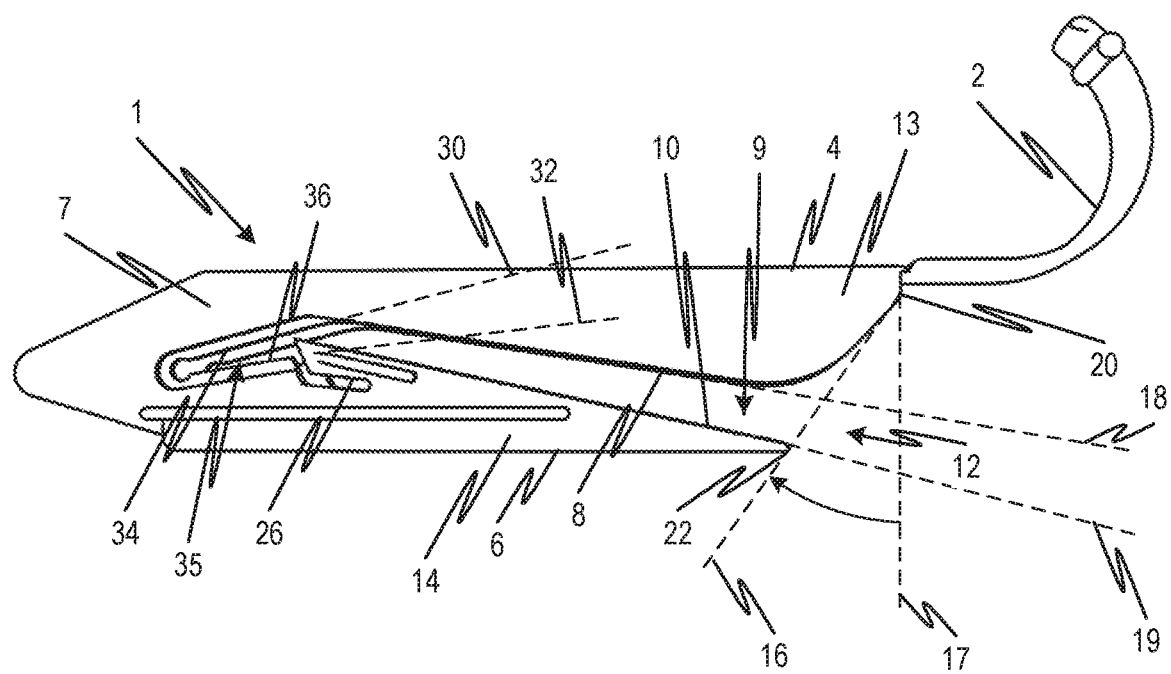
FIGS. 1A and 1B show a needle guard according to the prior art.
Figure 1B:
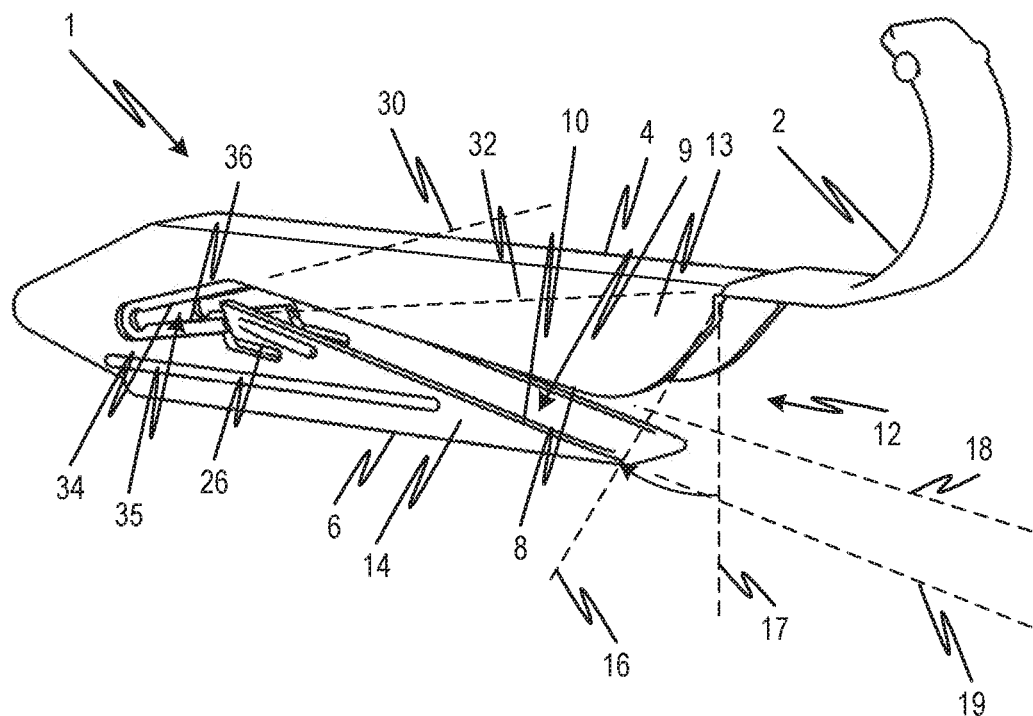
Figure 2A:
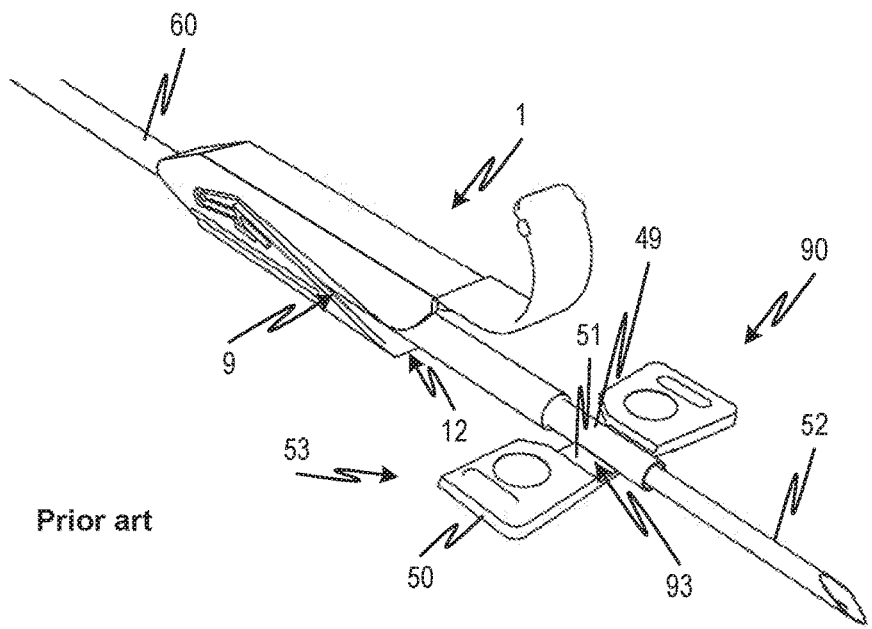
FIGS. 2A and 2B illustrate a method of using a prior art needle guard.
Figure 2B:
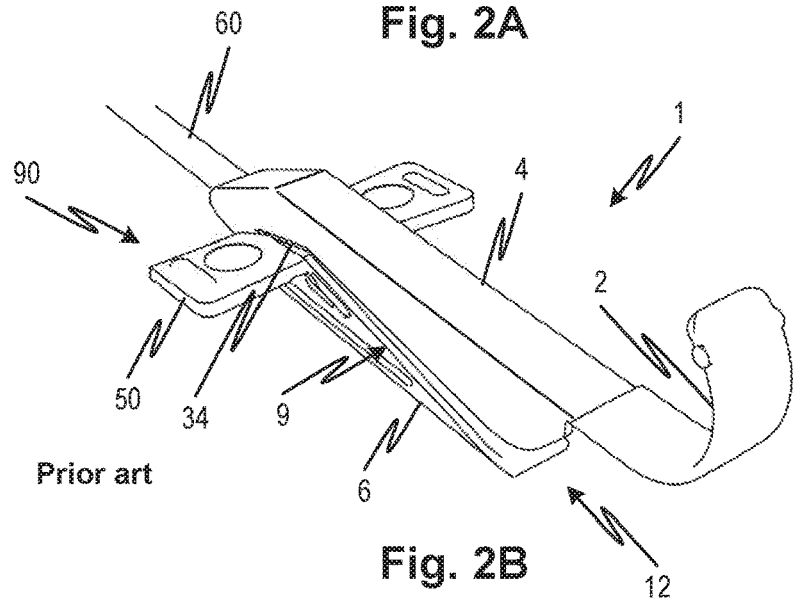
Figure 2C:
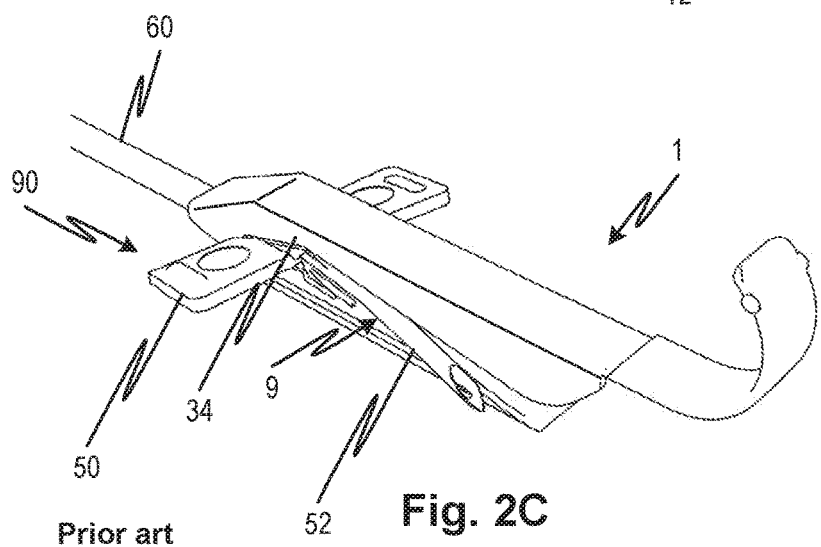
FIG. 2C illustrates an improper engagement of a needle with a needle guard according to the prior art.

Embodiments will hereinafter be described in detail below with reference to the accompanying drawings, wherein like reference numerals represent like elements.

Needle guards and needle sets according to embodiments of the disclosure prevent accidental punctures of users of the needle guard or caretakers of the users. In particular, features are provided to further protect against incorrectly sheathed needles, accidental contact with sheathed needles, and other problems with prior art needle guards.

Figure 4A:
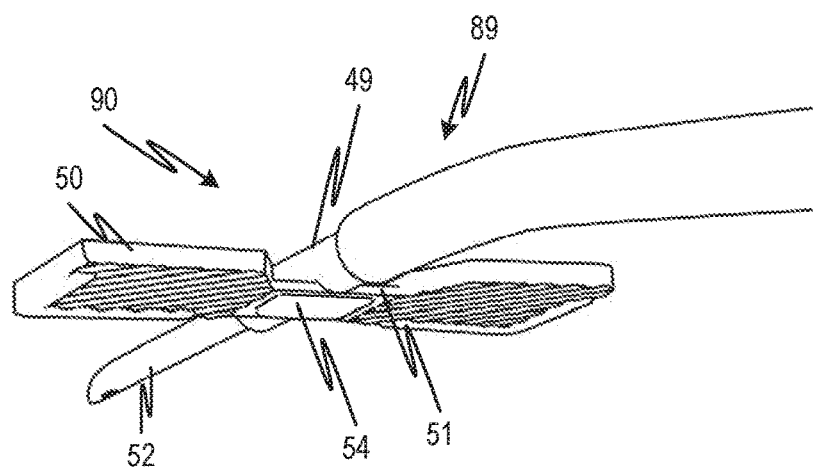
FIG. 4A illustrates a view of a winged needle according to embodiments of the disclosed subject matter.

Referring to FIG. 4A, a winged needle 90 includes a hub 49 which holds cannula 52. The hub 49 has wings 53 each of which includes two thin wing portions 51 extending laterally on substantially opposite sides of the hub 49. The thin wing portions 51 attach the hub 49 to thick wing portions 50, which are thicker than the thin wing portions 51. In embodiments the thickness difference is a factor of 2 or 3 or a number approximately in that range. The thin wing portion 51 may transition to the thick wing portion 50 progressively forming an inclined ramp 85 as shown in FIG. 7C. Alternatively, the transition may be abrupt forming a step (not shown). In either case, a valley 93 is defined between the side of the hub 49 and the thick wing portion 50. A similar valley may be formed on the bottom side of the winged needle 90 (not shown). The valley 93 may facilitate the retention and proper alignment of the hub 49 by providing interfering engagement between the step or ramp and the edges of the side walls 114 of the lower (and/or upper if such a valley is present) jaw 106 according to the respective embodiment.

Figure 3A:
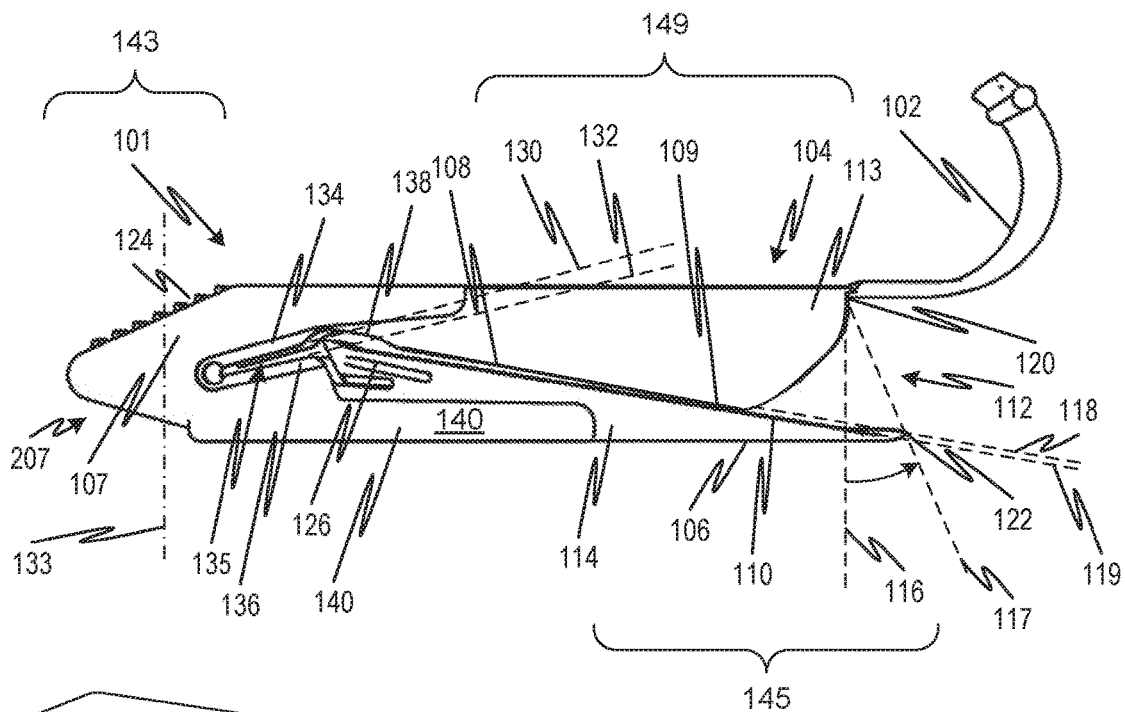
FIGS. 3A and 3B illustrate a needle guard according to embodiments of the disclosed subject matter.
Figure 3B:
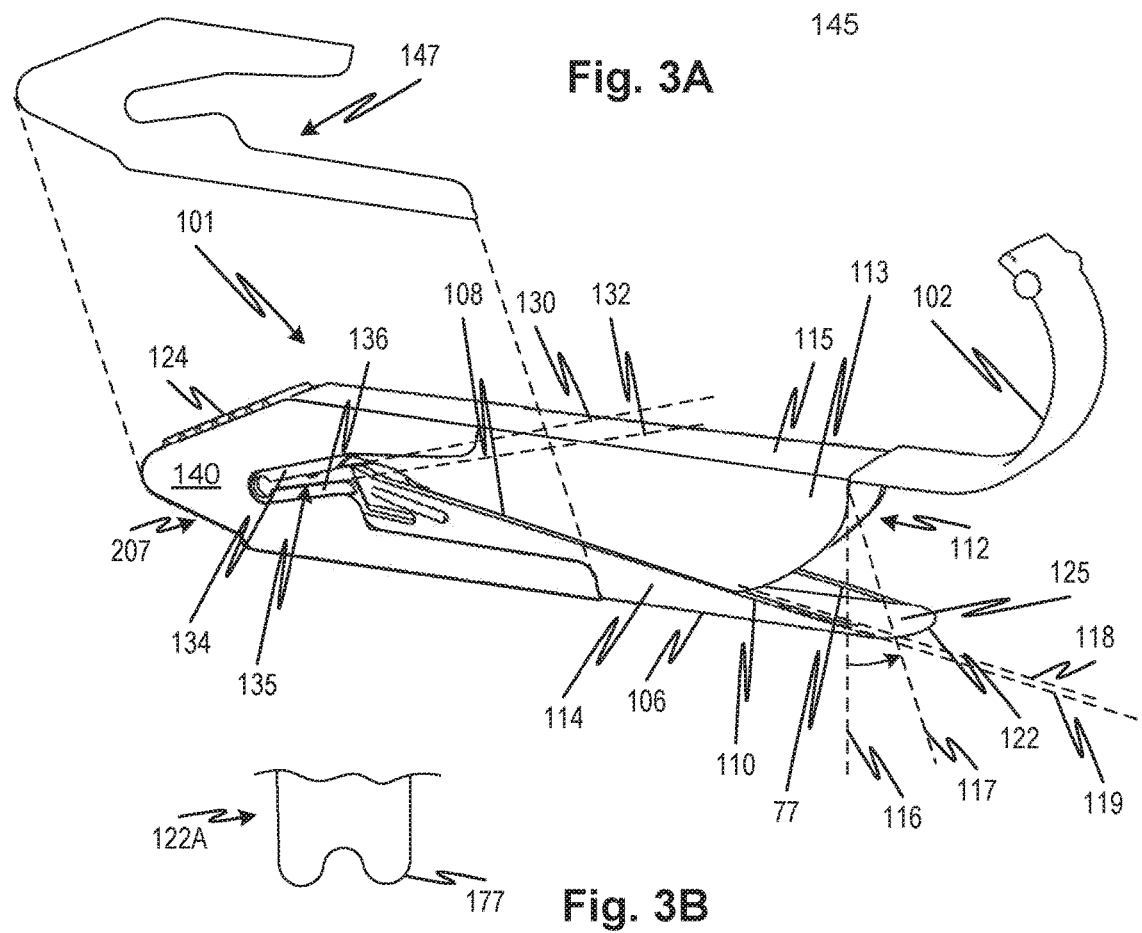

The bottom of the hub 49 and may include a nub 54 projecting downward as shown in FIG. 4A. The nub 54 is illustrated with a flat bottom surface and has a height measured down and away from the hub 49. Even though nub 54 is illustrated with a flat bottom surface, the bottom surface may have a more curved shape. The bottom surface shape of the nub 54 can be shaped to fit the space between side walls 114 of the lower jaw 106 of needle guard 101 as illustrated in FIGS. 3A-3B and discussed in more detail infra. Other shapes for a protrusion such as nub 54 may be provided, its function being to help align the winged needle 90 with a needle guard such as needle guard 101 discussed presently by providing an interfering engagement of the protrusion with the side wall 114 edge leading portion 77 on the lower jaw which may be inserted underneath the hub 49 to initially align the hub 49 with the needle guard 101. These features are shown in FIG. 4C.

Figure 4C:
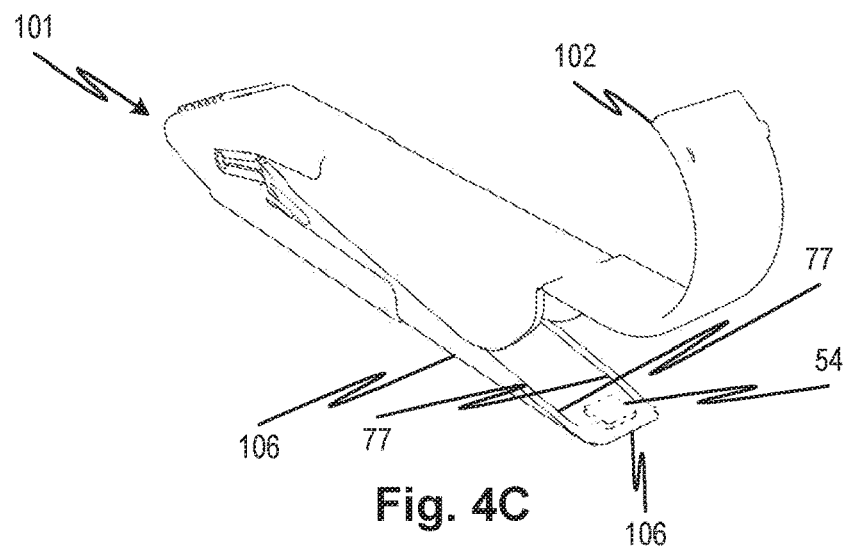
FIG. 4C shows a front view of the needle guard shown in FIG. 4B.
Figure 4B:
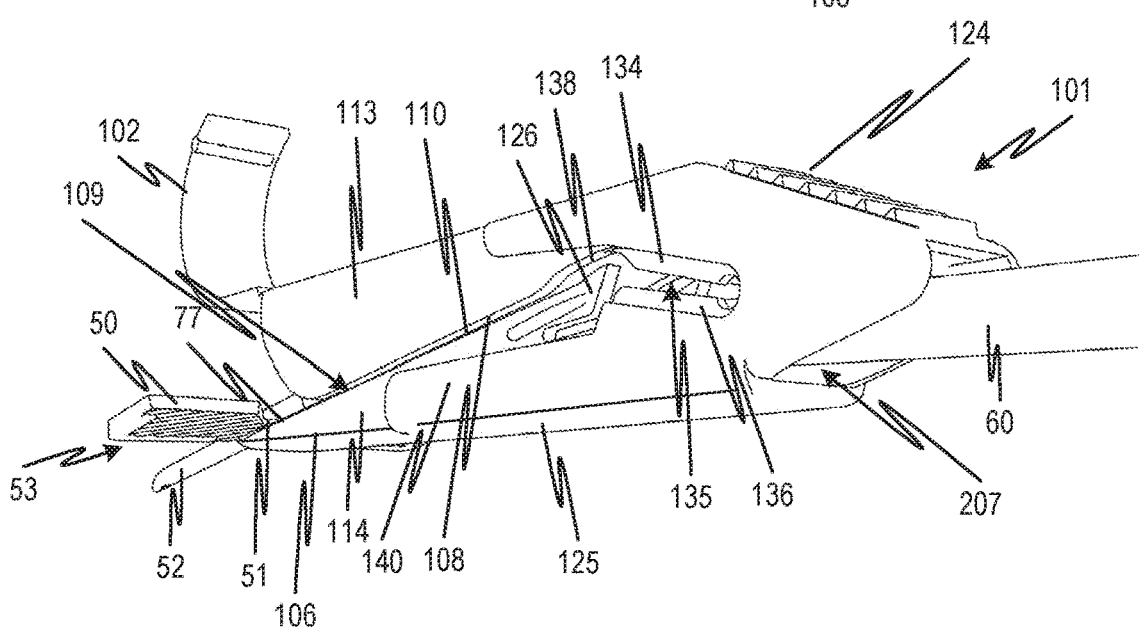
FIG. 4B illustrates a view of the winged needle of FIG. 4A being drawn into a needle guard according to embodiments of the disclosed subject matter.

Referring to FIGS. 4B and 4C, FIG. 4B illustrates the needle guard 101 in relation to the needle hub 49 at an initial time during a withdrawal procedure according to embodiments of the disclosed subject matter. A tube 60 passes through a rear opening 207 of the needle guard 101 and exits through the cavity 112 at the front end. This is a configuration of a needle set 89 that includes the winged needle 90 and needle guard 101 as part of the needle set 89. The user does not need to establish this configuration except for initially positioning the needle guard 101 with respect to the winged needle 90 by sliding the needle guard 101 along the tube 60. The tube 60 is connected to the winged needle 90. The winged needle 90 includes hub 49 and cannula 52. The cannula 52 is normally inserted at an appropriate site such as a patient's blood vessel, and the wings 53 of the hub 49 are attached to the patient with tape. When the cannula 52 is to be withdrawn from the patient, the needle guard 101 is manually held in place using the finger shield 102, raised ribs 124 located at the hinge region thereof, or a combination of these. The finger shield's 102 position, shape, and size are selected to permit pressure to be applied at the puncture site where the cannula 52 enters the patient's skin. When the needle guard 101 is in this position, the lower jaw 106 front edge 122 may be placed under the hub 49. If a protrusion such as nub 54 is present, it may be guided by the side wall 114 edge leading portion 77 as shown in FIG. 4C. As the tube 60 is pulled back, drawing the cannula 52 through the cavity 112 the wings 53 are guided into the slots 109 as shown, for example, in FIGS. 4B, 7A, and 7B. Thin wing portions 51 engage vertically with the front slot 109 while thick wing portions 50 remain horizontally outside the front slot 109 and provide horizontal stabilization due to interfering engagement with top edge 110 and/or bottom edge 108. In other words, the valley 93 may trap the bottom edge 108 of the upper side wall 113 and/or top edge 110 of the lower side wall 114 within it thereby steering the winged needle 90 straight (aligned with its axis parallel to the longitudinal axis of the needle guard 101) with respect to the needle guard 101. Again, at the same time, at least initially, the nub 54, in embodiments where present, may also be guided by the side wall 114 edge leading portion 77. Note that nub 54 is shown in FIG. 4C merely to show its position relative to the needle guard 101 when the lower jaw is inserted under the hub 49 having a nub 54. The drawing is not intended to show a disembodied nub or suggest that it is part of the lower jaw.

Note that in embodiments, the needle may be horizontally confined by a respective step or ramp in each of the wings as illustrated in FIG. 7C. That is the left inclined ramp 85 may prevent movement in the right direction and the right inclined ramp 85' may prevent movement in the left direction. Again the ramps may be steps and the limitation of movement is due to interfering engagement with the top edges 110.

The needle guard 101, according to embodiments of the disclosed subject matter, reduces the chances of cannula misalignment or other contact with a needle by providing a variety of features discussed herein, including:
  a. narrow slots that positively and interferingly engage the needle from an initial point of entry to the slots;
  b. increased lateral rigidity of the needle guard housing to prevent misalignment or failure of the slot edges to engage the needle;
  c. a lower jaw that protrudes beyond the upper jaw to facilitate the ability to plate the lower jaw beneath the needle hub prior to drawing the needle;
  d. an aperture at the front end that faces away from the needle tip as a result of an upward facing angle between the extended lower jaw and the upper jaw;
as well as other features.

FIGS. 3A and 3B show a needle guard 101 substantially as described with reference to FIGS. 4A through 4C. The needle guard 101 may prevent accidental punctures even when the user pulls the tubing at an angle relative to the needle guard 101. The needle guard 101 has slots defined by top 110 and bottom 108 edges that may be substantially parallel or linearly converging from a position near the back of the needle guard 101 to the front of the needle guard 101. FIGS. 4A and 4B show an embodiment in which the top 110 and bottom 108 edges are parallel. FIGS. 3A and 3B show an embodiment where these edges are not parallel but define a converging slot that defines a gap that is zero at the front end and the thickness of a wing of the winged needle at the other end. Either type of slot converging or parallel, may be provided in any of the embodiments. The upper and lower jaws may be such that the edges overlap, touch, converge but rest just short of touching, depending on the degree of convergence. Some degree of lateral offset of the edges of the upper jaw relative to the lower may be permitted to allow overlap, such as by making one of them slightly wider.

The slot may be made to converge by the structure of the guard and the process of cooling the part from a mold where the thickening of the needle guard 101 at the hinge end causes the upper and lower jaws to close due to slower cooling at the back part of the hinge portion than the front part of the hinge portion. This difference in cooling may be caused by the additional reinforcement provided by the thickened region 140. The needle guard 101 is also made rigid through thickening of certain portions that affect the flexibility of the needle guard 101. The narrower slot and the increased rigidity make it more difficult for the tubing of the needle assembly to fit between the lower jaw and the upper jaw. Thus the combination of the thicker rear portion of the needle guard 101 and the parallel or converging slots prevent escape of the needle by providing rigidity that keeps edges defining the slots aligned laterally and causing cooling of the front side of the hinge region faster than the heaver read side of the hinge region. Further the limited width of the slot as compared to the prior art prevents the escape of the needle as well. It is more difficult for the needle to become wedged into the slot than in the prior art configuration. To further enhance the rigidity, the choice of materials may be suitably limited. In embodiments the material may be a rigid polymer as indicated herein. The increased rigidity and narrower slot guides and secures the needle wings 53 during the entire removal of the needle, from the initial point of contact between thin wing portion 51 and the jaws until the wings 53 are securely locked in the rear slot 135, to avoid the sharp needle tip extending out the slot opening, avoiding an accidental needle puncture.

The needle guard 101 has an upper jaw 104 and lower jaw 106 joined at hinge 107 and formed in a monolithic structure, defining a cavity 112 with slots on either side. The slots include a front slot 109 and rear slot 135 being defined by the bottom edge 108 of the side wall 113 of the upper jaw 104 and the top edge 110 of the side wall 114 of the lower jaw 106. The front slot 109 may be called the receiving slot.

As may be seen in the drawing, the front slots 109 (one on either side) have a constant, or nearly constant width such that the upper jaw side wall 113 bottom edges 108 and lower jaw side wall 114 top edges 110 are parallel (indicated by the projecting lines 118 and 119). Further, the size of the slots is narrow as indicated by the spacing between projecting lines 118 and 119. In embodiments, the slot spacing can be as narrow, or narrower than, the thickness of the thin wing portion 51, which keeps the cannula 52 contained between the slots.

Upper jaw 104 includes as substantially flat roof 115 and two opposed side walls 113 extending down from the roof 115. Though roof 115 is illustrated as flat, it may be curved or have a triangular cross-section in different embodiments which may be combined with all of the embodiments discussed below. The curved roof or the triangular cross-section roof may guide the sharp point of the cannula to a point and resist sideways movement of the cannula point.

Each side wall 113 has a substantially straight upper edge integral with the roof 115 and extending down from roof 115. The front end of the side wall 113 is curved from the front end 120 to a straight bottom edge 108. The bottom edge 108 extends to and abuts the bridge slot 138 as illustrated in FIGS. 3A and 8A.

Side wall 113 does not have a uniform thickness. Instead, the side wall has a one thickness at the front end and includes a thickened region 140 at the rear end (toward the rear of the needle guard 101 shown on the left side of FIG. 3A). The thickened region 140 extends from the upper jaw side wall 113 through the hinge 107 to the lower jaw side wall 114. The thickened region has a thickness that is greater than the thickness of the side wall 113 and side wall 114 at the front end. The thickened region 140 of the needle guard 101 increases the stiffness of the part and minimizes the lateral bending of the upper and lower jaws. This lateral movement can cause the slot to open, allowing the needle tubing to wedge open the slot and thus creates the aforementioned condition of the cannula being exposed. The thickness of the wall may be greater than 1 mm. In embodiments, the wall is 1.25 mm in the thickened rear section of the guard. In embodiments, the thin and thick sections are 0.8 mm and 1.4 mm, respectively.

The roof 115 of the upper jaw extends from the front of the needle guard 101 toward the hinge 107, joining the roof of the hinge 107. The hinge 107 has two side walls and two rear slots 135 on opposite sides, as shown in FIGS. 3A and 3B. The rear slot 135 is defined between edges 134 and 136 that also taper as indicated by projections 130 and 132 that are aligned with the edges 134 and 136. The rear slot 135 receives wings of a winged needle as discussed below. The edges 134 and 136 form an acute angle as indicated by the projections 130 and 132 of the edges 134 and 136. The rear end of rear slot 135 terminates in a partial circle. A resilient latch 126 is formed on the lower jaw side wall 114 to catch the wings of a winged needle drawn into the rear slot 135.

The edges 134 and 136 have a height (measured in the direction substantially perpendicular to roof 115) which is substantially equal or greater than the thickness of the thick wing portion 50. This enables the edges 134 and/or 136 to mate with the valley 93 formed above thin wing portion 51. The thick wing portions 50 remain on the outside of the edges 134 and 136 acting as fences to maintain the correct alignment of the needle inside the needle guard 101. The rear slot 135 abuts a bridge slot 138 which in turn abuts the front slot 109, as shown in FIGS. 3A, 3B, and 8A.

The bridge slot 138 projects beyond the point where the extension of the bottom edge 108 and the extension of edge 134 would intersect, as shown in FIG. 8A. The bridge slot 138 thus creates an enlarged space, void, recess, or cavity above the resilient latch 126. The bridge slot 138 has a length d from one end (where it abuts the rear slot 135) to an opposite end (where it abuts the front slot 109) that is at least as long as the length of the cross-section of thin wing portion 51, as shown in FIG. 8A. The bridge slot 138 creates a recess at a location between the front slot 109 and the rear slot 135 that provides more space for the thin wing portion 51 to traverse from the front slot 109 to the rear slot 135. The process of the thin wing portion 51 traversing the slots is illustrated in FIG. 8A-8F, showing the thin wing portion 51 progressing through positions as it moves from the front slot 109 at the front of the needle guard 101 to the rear slot 135 at the rear of the needle guard 101.

The recess created by the bridge slot 138 is an open space or a void above the resilient latch 126. This void has a large aspect ratio such that the length d is greater than the height of the void measured form the top of the resilient latch 126 to the roof of the bridge slot 138. In an embodiment of the disclosed subject matter the aspect ratio of the recess or void created by the bridge slot 138 above the resilient latch 126 is 2. In an embodiment the aspect ratio is greater than 2. In an embodiment the aspect ratio is greater than or equal to 3. In an embodiment the aspect ratio is greater than or equal to 4.

In an embodiment, the height of the open space created by the bridge slot 138 measured from the top of the resilient latch 126 (at the base of barb 127) is greater than the height of the thin wing portion 51, as shown by the free space above and below the thin wing portion 51 in FIG. 8A. In an embodiment, the height of the open space above the upper tip of barb 127 is equal to or smaller than the height of the thin wing portion 51, so that the thin wing portion 51 causes the resilient latch 126 to deflect downward when the thin wing portion 51 traverses the bridge slot 138 and presses on the barb 127.

The bridge slot 138 has serpentine shape helps to resist the needle wings moving forward out of the rear slot 135 by bypassing the resilient latch 126. The bridge slot 138 allows the front slot 109 and the rear slot 135 to be narrow, while allowing the thin wing portion 51 to smoothly make the turn from the front slot 109 to the rear slot 135. The shape of the recess formed by the bridge slot 138 provides for a smooth and consistent pull of the winged needle 90 through the needle guard 101. In an embodiment, the force required to be exerted on the tube 60 to pull the winged needle 90 through the needle guard 101 is constant through the pull from the point where the thin wing portion 51 first engages the front slot 109 until the thin wing portion 51 arrives at the rear end of the rear slot 135 and its progress is blocked by the rounded end of the rear slot 135. The pulling force is based on the coefficient of friction between the straight bottom edge 108 and the top edge 110 pinching the thin wing portion 51 and on the force required to deflect the resilient latch 126 when the thin wing portion 51 traverses the bridge slot 138. When the thin wing portion 51 first enters the front slot 109, the pinching force of the straight bottom edge 108 and the top edge 110 is the only force contributing to the pulling force on the tube 60. When the thin wing portion 51 reaches the bridge slot 138, as shown in FIG. 8A, the pinching force of the straight bottom edge 108 and the top edge 110 is exerted on only a small trailing portion of the thin wing portion 51. At that point, the force to depress the resilient latch 126 compensates for the decrease of the pinching force exerted by the straight bottom edge 108 and the top edge 110, providing for a substantially constant pulling force on the tube 60. Providing a substantially constant pulling force provides a smooth and easily repeatable motion for the user of the needle guard 101. It is safer to use a needle guard 101, or any sharp object for that matter, when jarring or jerking movements are avoided.

Resilient latch 126 is partially an extension of the top edge 110 of the side wall 114 of the lower jaw 106, as shown in FIG. 8A. The resilient latch 126 includes a barb 127 at its rear end, as shown in FIG. 8A. Thus, the upper edge of the resilient latch 126 is not straight, but has a bend or a kink upward to the tip of barb 127. The upper edge of the resilient latch 126 has a hockey stick shape. The hockey stick shape creates a larger space between the bridge slot 138 and the resilient latch 126 as compared to an embodiment that lacks the hockey stick shape. Although FIG. 8A illustrates the upward kink of barb 127 as having straight sides, the kink can be formed with an upward curving edge, curving up from an extension of the top edge 110 toward the sharp tip or point of the barb 127.

The resilient latch 126 is capable of movement down toward the lower jaw in response to force from the direction of the upper jaw, but it springs back. The resilient latch 126 is positioned such that the cross section of thin wing portion 51 can pass through the bridge slot 138 while the thin wing portion 51 depresses the resilient latch 126, as shown in FIGS. 8A-8F. In FIGS. 8A-8F, a cross section of thin wing portion 51 is shown in sequence as it presses down on the resilient latch 126 and passes though bridge slot 138. The bridge slot 138 creates a clearance space for the thin wing portion 51 above the upper edge of the resilient latch 126.

In FIG. 8C the resilient latch 126 is pressed down, but is springs back to its original position once the thin wing portion 51 slides beyond the resilient latch 126, as shown in FIG. 8F. The resilient latch 126 is resilient and springy such that it springs back with speed and force once the thin wing portion 51 passes beyond it. This springing back is like strumming a guitar string and creates an audible and also palpable sensation (a click) for the user of the needle guard 101. The audible and palpable feedback confirm to the user that the needle 90 has been correctly retracted, improving the safety of the device. If the user does not hear and/or feel the expected feedback, the user will check closely to ensure that the needle has been retracted and reduce the likelihood of an accidental puncture.

The audible and palpable feedback is increased by barb 127 which makes the resilient latch 126 effectively taller, causing the thin wing portion 51 to press the resilient latch 126 down farther than if there was no barb. The additional depressing of the latch causes the latch to spring back with more force and increases the feedback for easier perception by the user. The barb 127 also provides a taller obstacle for the thin wing portion 51 once it has passed into the rear slot 135. Any reverse movement (i.e., from the rear of the needle guard 101 toward its front) is blocked by the barb 127. Moreover, the use of barb 127, instead of making the entirety of the resilient latch 126 taller, allows the resilient latch 126 to maintain springiness and maintain a smooth and continuous pulling motion for pulling winged needle 90 into the needle guard 101. If the resilient latch 126 were made taller in its entirety, it would become more difficult for the thin wing portion 51 to deform the latch 126 as thin wing portion 51 travels through the slot.

Referring now to FIG. 8G, a projection of the rear slot 135 is indicated by lines 139A and 139B. It will be observed that the tip portion 137 spans the entire of this projection indicating that the path for exit of the thin wing portion 51 is effectively blocked by it. Since there is no path guide that can deform the thin wing portion 51 such as a curved wall that could guide a leading edge of thin wing portion 51 over the latch 126, the thin wing portion 51 is effectively blocked by the latch 126. This contrasts with the prior art rear slot 35 which is only partially blocked. Also, the rear slot 135 is approximately the same width as the thin wing portion 51. This is compared to the rear slot 35 which is substantially larger than the thin wing portion 51. In addition, the bridge slot 138 transition to the rear slot 135 has a wall section 153 that curves down forming an acute angle with the walls of the rear slot 135. The thin wing portion 51 is thus guided down toward the rear slot 135 (See FIG. 8C) in a direction lateral to the walls of the rear slot 135 defining a relaxed S-curve or chicane in the path defined by the front slot 109, bridge slot 138, and rear slot 135. The wall section 153 pushes the thin wing portion 51 against the latch 126 causing it to retract (FIGS. 8B to 8C).

Referring again to FIG. 8G, it may also be observed that the front slot 109, bridge slot 138, and rear slot 135 have respective axes front slot axis 171, bridge slot axis 172, and rear slot axis 173. The front slot axis 171 and bridge slot axis 172 are parallel but not collinear. It may also be observed that the transition from the bridge slot 138 to the rear slot 135 defines an S-shaped path around the latch 126 tip portion 137. In terms of paths, the transitions through front slot 109, bridge slot 138, and rear slot 135 may be described as a jog followed by an S-shaped bend as shown in FIG. 8J.

As shown in FIGS. 3A and 3B, the edges 134 and 136 are of a reduced thickness (measured in the direction perpendicular to the side walls 113 and 114) relative to the thickened region 140, which bounds the edges 134 and 136. One effect of this difference in thickness is that upon molding or casting of the needle guard out of a polymer material, the material at edges 134 and 136 cools faster than the material in the thickened region which surrounds edges 134 and 136. The material that cools faster shrinks and creates tension in the surrounding material which, due to cooling more slowly, is still soft and pliable. The tension in the thinner material pulls on the still-pliable material, causing the hinge to partially close as it cools. The partial closing of the hinge pulls the lower jaw against the upper jaw, biasing them against each other. Once the thickened portion cools, the material solidifies, setting its shape, and the bias of the upper jaw against the lower jaw persists. This process may be characterized as one where the jaws close slightly. This effect may create the converging shape of the slots. Note also that as a result of this jaw-closing, the draft of the inside of the needle guard 101 may be reduced and even be negative. That is, the hollow inside of the needle guard is formed in molding by a three-part mold including two molds that converge toward the longitudinal axis of the molded part (i.e., the needle guard 101) and a core that fits inside and is drawn out of the front. In the embodiments shown, the core may have a zero or positive draft such that it can be pulled out of the molded part. If the part cools in the manner described, the internal draft angles will be reduced and may even be negative. As shown in FIG. 3A, this biasing causes the upper jaw and the lower jaw to come in contact at least at the front end of the needle guard 101.

Figure 7D:
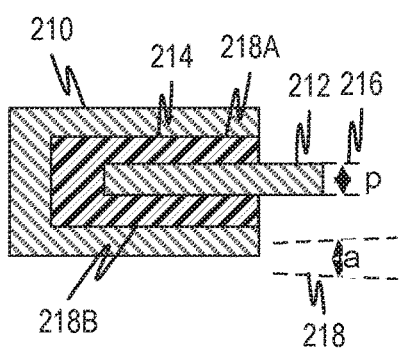
FIGS. 7D and 7E illustrate aspects of the molding operation for a needle guard according to embodiments of the disclosed subject matter.
Figure 7E:
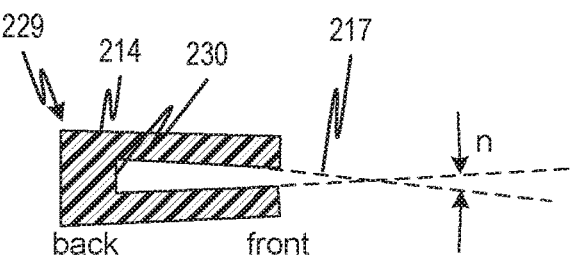

To illustrate the terms and concepts described consider a molded hollow part 214 as shown in FIG. 7D. The mold 210 may be a two-part mold that releases the part 214 (with legs 218A and 218B) in a direction normal to a plane of the page. A core 212 is inserted making the assembly a three-part mold with two actions (the splitting of the mold parts 210 and the withdrawal of the core 212. In order for the core to be removable from the part 214 the core 212 has to be shaped with a neutral (angle p=0) or positive (angle a=a positive number) draft. If the part 214 is a needle guard of any of the embodiments, and the core has a neutral or near-zero draft, then the opening may be characterized by a negative draft after cooling it causes the legs 218A and 218B to converge (angle n) as shown by converging rays 217 in FIG. 7E. Thus, the part 214 may have an internal draft angle (or shape) that is negative as a result of being cooled in a manner that causes its shape to change in this way. In embodiments, the needle guard 101 is molded and the mold shape configured such that the part cools after release from the mold such that the thicker walled hinge portion is still somewhat plastic as portion of the hinge portion toward the front cools and shrinks. The part 214 is a simplified version of the needle guard molded part. In part 214 the hinge portion would correspond the portion indicated at 229 and the front of the hinge portion would be the portion at 230. If the front of the hinge portion is thinner or otherwise cools faster after release from the mold (or is cooled differently inside the mold such as by heat transfer mechanism) so that the front part cools and shrinks first, then the negative draft (or more negative draft than a positive draft of the mold core itself) would be obtained. Other ways to make the jaws "close" are also possible such as by mechanically deforming while the part is still plastic or placing an external spring or other urging mechanism on the part after molding.

In other embodiments, it possible to make the separation between the upper jaw and the lower jaws for a needle guard correspond to the thickness of the wings or such portion thereof that fits into the slot such that there is a tight but reasonably low friction engagement between the needle guard edges and the wings. In such embodiments the jaws might not touch at the front end, but the front slot may taper away from the hinge toward the front end. When the thin wing portion 51 is at least as thick as the height of the front slot 109 at its front end and also at least as thick as the maximum height of the front slot 109, the upper jaw 104 and the lower jaw 106 will grip the winged needle 90 firmly but without producing significant friction as it is pulled through the needle guard 101, avoiding sideways misalignment of the winged needle 90. The tightness need only be sufficient to ensure positive interfering engagement and does not need to actually grip the wings if the interfering engagement, such as between the inclined ramp 85 (or step—not shown) and the edge 110. Note also that the interfering engagement between the slot edge and wing can be provided between the top edge and a feature such as a step or inclined ramp on the upper surface of the wing, between the bottom edge and a feature such as a step or inclined ramp on the lower surface of the wing, or both.

Figure 6A:
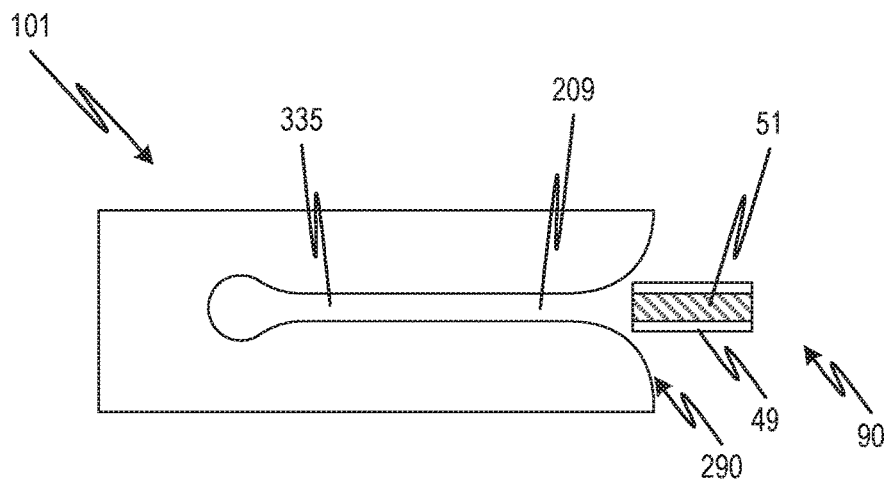
FIGS. 6A and 6B show an abstract illustration of a needle guard whose features are exaggerated to illustrate the engagement between a needle guard and wings of a needle hub according to embodiments of the disclosed subject matter.
Figure 6B:
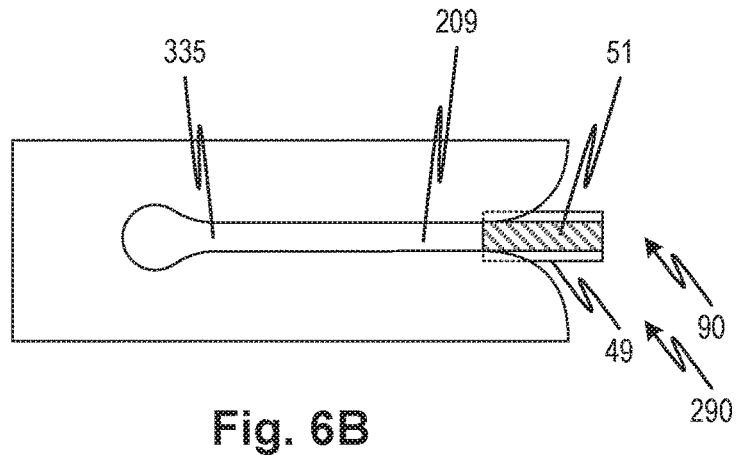

FIGS. 6A and 6B illustrate a simplified representation of a needle guard 101 with front slot 209 and rear slot 335. The front slot 209 has an opening that is large enough to accommodate the winged needle 90 without it being pried open. However, a step or inclined ramp 85 may engage the edges and guide the winged needle 90 throughout a length of the front slot 209 and rear slot 335. A progressively narrowing entrance 290 to the front slot 209 is shown which provides for a smooth capture (FIG. 6B) and engagement of the winged needle thin wing portion 51.

Figure 7A:
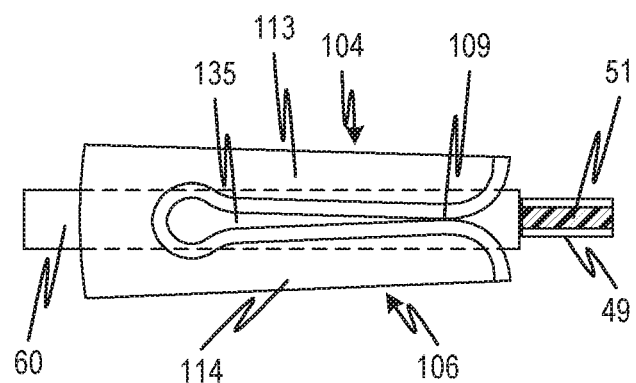
FIGS. 7A and 7B show an abstract illustration of a needle guard whose features are exaggerated to illustrate the shape of the guard and the engagement between the guard and needle according to embodiments of the disclosed subject matter and wings of a needle hub.

FIG. 7A shows a simplified representation of the front slot 109 and the rear slot 135 of an embodiment of the disclosed subject matter as a single slot, with a front end of the upper and lower jaws coming into contact. While FIG. 7A is not drawn to scale and omits the resilient latch 126 and bridge slot 138 for clarity, it illustrates the biasing of the two jaws against each other. Tube 60 of the winged needle passes freely through cavity 112. FIG. 7A shows a cross-section of thin wing portion 51 which extends from winged hub 49 to the thick wing portion 50. The thin wing portion 51 is shown as a cross-section but it understood that the thick wing portion 50 may be present as in the other embodiments. Note that the wings can be of any configuration depending the embodiment, and preferably the wings have an engagement edge suitable to confine the hub to a central path through the needle guard.

Figure 7B:
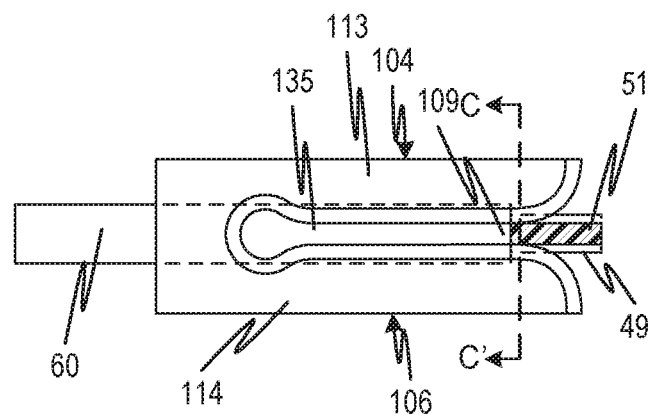
Figure 7C:
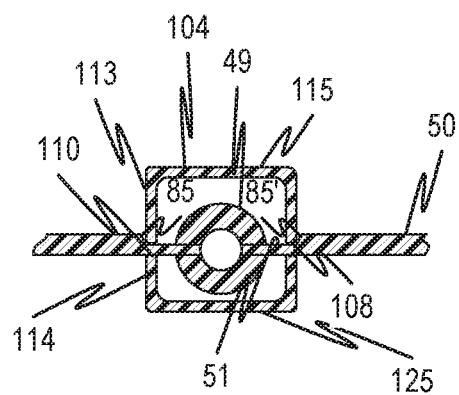
FIG. 7C illustrates a cross-sectional view across plane C-C' in FIG. 7B.

As tube 60 is pulled in the direction from the front end of the needle guard 101 toward the rear end of the needle guard 101, the thin wing portion 51 comes into contact with the lower jaw 106 and with upper jaw 104 and pries them apart as shown in FIG. 7B. Because the jaws are biased against each other, they exert a force from opposed sides on the thin wing portion 51, keeping the winged needle 90 properly aligned with the front slot 109 for the entire traversal of the winged needle 90 through the front slot 109 and the rear slot 135.

FIG. 7C shows a cross-sectional view between points C and C', looking into cavity 112 when the thin wing portion 51 has pried apart the upper jaw 104 and the lower jaw 106. As seen in FIG. 7C, the jaws maintain contact with the thin wing portion 51. The thick wing portion 50 is thicker than the thin wing portion 51 and thus creates a wall on the outside of the front slot 109, avoiding sideways translation or rotation of winged needle 90, so the cannula 52 remains safely within cavity 112.

As shown in FIG. 3A, the top outer surface of the hinge 107 includes raised ribs 124 extending generally perpendicularly to the longitudinal axis of the needle guard 101. The raised ribs 124 provide a secure grip for a user of the needle guard 101. A user may press on raised ribs 124 to hold the needle guard 101 in place while pulling on tube 60 to retract the winged needle 90. Although parallel ribs are illustrated in the figures, a different pattern that improves the user's comfort and provides a more secure grip can be used, including cross hatches, stippling, and a roughened surface. The raised ribs 124 address the needs of different user approaches to holding the needle guard 101 in place as the needle is drawn back. Some users prefer the safety of keeping fingers away from the front of the needle guard 101 and there for avoid using the finger shield 102. To provide such users with a more secure grip on the needle guard 101, the raised ribs 124 are provided which not only increase grip, but also provide feedback to the user of the position of the user's fingers relative to the needle guard 101. The positioning of the raised ribs 124 at the back end on a sloping surface makes it easier for the user to locate the position by feel. Also, the security provided by pressing on the sloping surface is increased because the surface faces away from the traction forces that need to be applied to pull the winged needle through the slots and the latch (described below).

As mentioned above, the hinge 107 abuts the lower jaw 106. Lower jaw 106 includes two opposed side walls 114 joined to floor 125. As shown in FIGS. 3A and 3B, front end 122 of the lower jaw 106 extends beyond the front end 120 of the upper jaw 108 as indicated by the angle formed between a line 117 that is perpendicular to the needle guard 101 major axis and a line 116 connecting the front end 122 of the lower jaw 106 to front end 120 of the upper jaw 104. The front end 122 may have rounded shape for increased comfort when the lower jaw is pressed against a patient's skin. The front end 122 may also be straight. In embodiments, the front end 122 has a notch in the center of the front end, resulting in a two-pronged fork that can straddle the cannula 52 from two sides when the cannula 52 is withdrawn from the patient and help guide the winged needle 90 into cavity 112. Preferably such a front edge would be rounded, for example defining a "B" shaped front end 122A as indicated at 177. The extended lower jaw has the additional effect of reducing the intensity of the force to the skin at the front end 122 resulting from leveraged forces applied to the finger shield 102. In the prior art needle guard 1 and the disclosed embodiments 101, the magnitude of leverage applied against the skin is greater than unity due to the significant overhang of finger shield 102. In the disclosed embodiments, the lower jaw 106 is extended to the point where it underlies region where the finger is placed for removal of the winged needle 90. Comfort may further be increased by providing that there is a convex bevel 1401 at the forward end of the lower jaw as shown in FIG. 14B.

The side wall 114 of the lower jaw 106 may have a non-uniform thickness with a thickened region 140 discussed above. The thickened region 140 improves resistance to lateral movement of the lower jaw 106 relative to the upper jaw 104 so that a thinner region forward thereof may permit greater economy in the use of polymer where the flexion is less of an issue. The shape of the thickened region is indicated at 147, which is not intended to indicate that it is a separate part but merely an outline to highlight the boundaries of the portion indicated at 140. The thickened region 140 is located at the rear end (hinge end) because the weakest point in the lateral movement of the upper and lower jaws is the hinge region. The channel shaped upper and lower jaws form trusses that have reasonably good resistance to bending even if the walls are thin over at least a portion thereof. The upper jaw has higher depending walls and can tolerate a longer thin span indicated at 149. The lower wall having lower depending walls is reinforced by thickened region 140 further toward the front end of the needle guard 101 so that there is a shorter thin region 145. The hinge arc in back experiences a torsional twisting moment about a vertical axis 133 which is harder to resist with the hollow structure especially with the presence of the opening 207 (See FIG. 4B). Thus, the hinge portion 143 is reinforced by thickened walls.

Figure 5A:
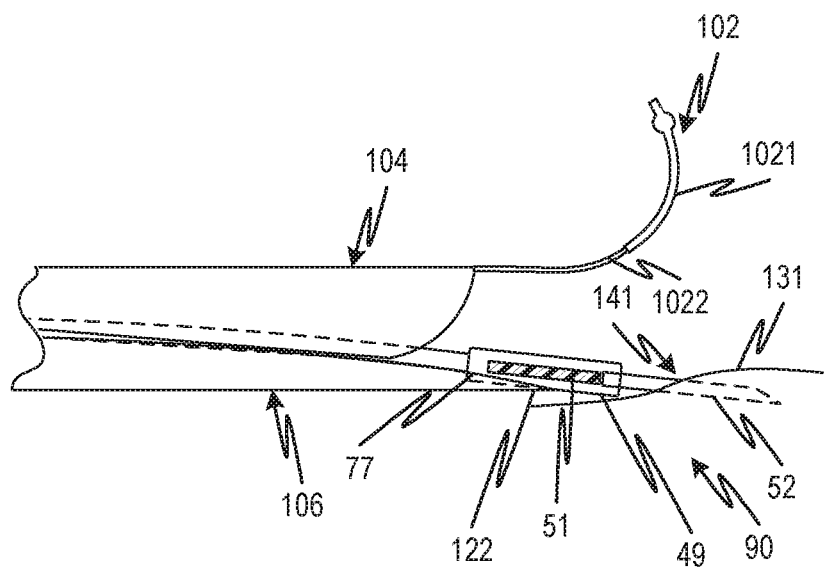
FIGS. 5A and 5B illustrate features of a needle guard as well a method of use of a needle guard according to embodiments of the disclosed subject matter.
Figure 5B:
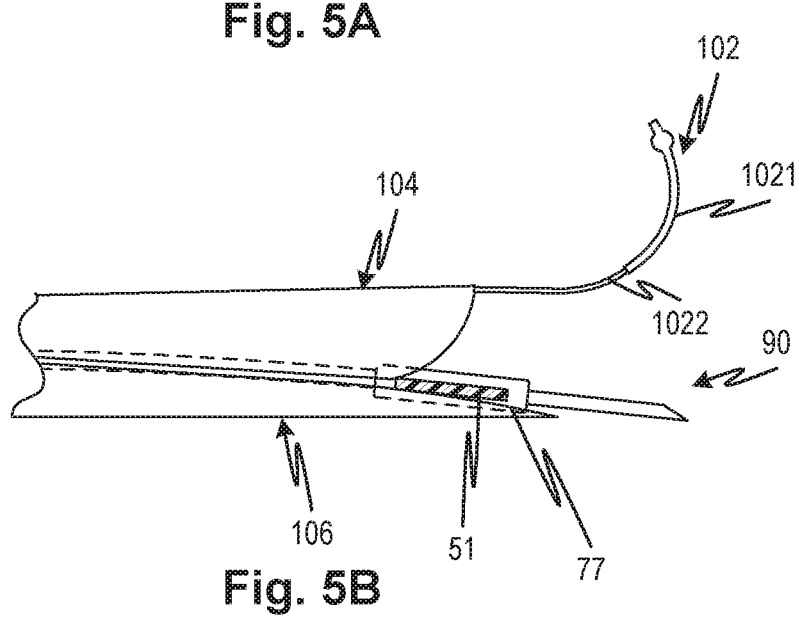

Referring also to FIGS. 5A and 5B, the extended lower jaw 106 of the needle guard 101 permits the convenient placement of the front end 122 of the lower jaw under the needle hub 49 adjacent a needle puncture site 141 of a patient's body 131. This allows the positioning the finger shield 102 above the puncture site 141. This helps to ensure the hub (nub 54 or equivalent, if present) is, prior to drawing, positioned between the 122A side wall 114 edge leading portion 77 as indicated at 122A as indicated at 177, as shown in FIG. 3B. The extended length of the lower jaw 106 facilitates the accurate placement of the finger shield 102 directly over the needle puncture site 141, providing for precise placement of gauze holding pressure fingers over the needle puncture site 141 to control bleeding. The front end 122 of the lower jaw 106 may be positioned immediately adjacent, and optionally beneath, gauze bandage covering the needle puncture site such that side walls 114 provide stabilization for the thick wing portion 50 and thin wing portions 51 immediately when the needle is pulled out and pulled through the needle guard 101, as shown in FIG. 5B. Further, the extended length places the needle wings in the precise position for guiding needle wings into the slots.

Figure 5C:
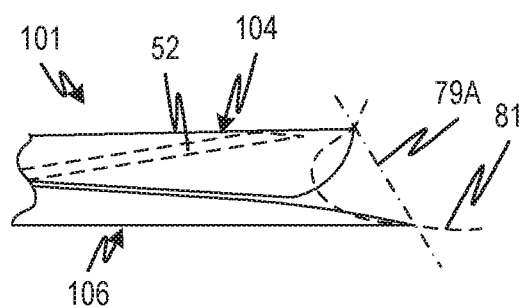
FIGS. 5C and 5D illustrate a feature of an extended lower jaw of the disclosed embodiments by comparing an embodiment 5C of the disclosed subject matter with a prior art needle guard 5D.
Figure 5D:
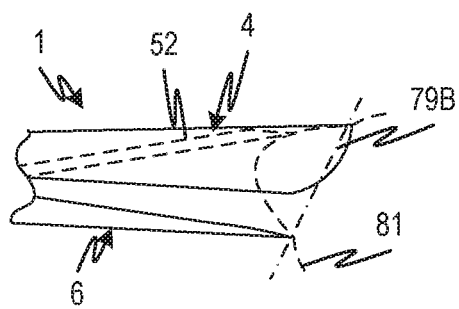

Additionally, the extended lower jaw reduces ease with which a user can inadvertently insert the finger into the cavity 112 within close proximity of the locked needle tip. Referring to FIGS. 5C and 5D, the needle guard 101 with an extended lower jaw 106 is shown in FIG. 5C and a needle guard 1 of the prior art with a shorter lower jaw 6 is shown in FIG. 5D. The aperture defined by the relationship between the upper 104 and lower 106 jaws of needle guard 101 of the disclosed subject matter faces upwardly as indicated by the plane 79A which extends into the page. A soft body part 81 pressed against this aperture, such as the tip of a finger, may extend past the aperture but it extends in a direction away from the tip of the cannula 52 in its stored position. The aperture defined by the relationship between the upper 4 and lower 6 jaws of needle guard 1 of the prior art faces downwardly as indicated by the plane 79B which also extends into the page. A soft body part 81 pressed against this aperture, such as the tip of a finger, may extend past the aperture in a direction toward from the tip of the cannula 52 in its stored position. This creates a risk of inadvertent needle stick or contact with the needle or fluids thereon. Thus, by extending the lower jaw relative to the upper jaw and the degree to which the lower jaw extends beyond the upper jaw, the disclosed subject matter defines an aperture that points at least partially away from the position of the tip of a needle in the locked and stored position.

Referring to FIGS. 5A and 5B, the finger shield 102 is extends from the front end 120 of upper jaw 104. The finger shield 102 may be integrally formed with the roof 115 of the upper jaw 104 or may be attached to the upper jaw 104 as a separate component. The finger shield 102 facilitates holding the needle guard 101 in position while the needle is drawn into it. As shown in FIGS. 5A and 5B, the shield 102 has a thin portion 1022 and a thick portion 1021. The thick portion 1021 is thicker than the thin portion 1022, and is thus less flexible. This allows the finger shield 102 to maintain its shape so that it curls around a user's fingertip even when the user presses down into the curve of the finger shield 102 toward a gauze place above the cannula 52 puncture site. This helps to ensure the finger shield 102 continues to hook the finger of the user to help resist the traction forces applied to the needle guard 191 as the winged needle 90 is drawn into it.

Figure 14A:
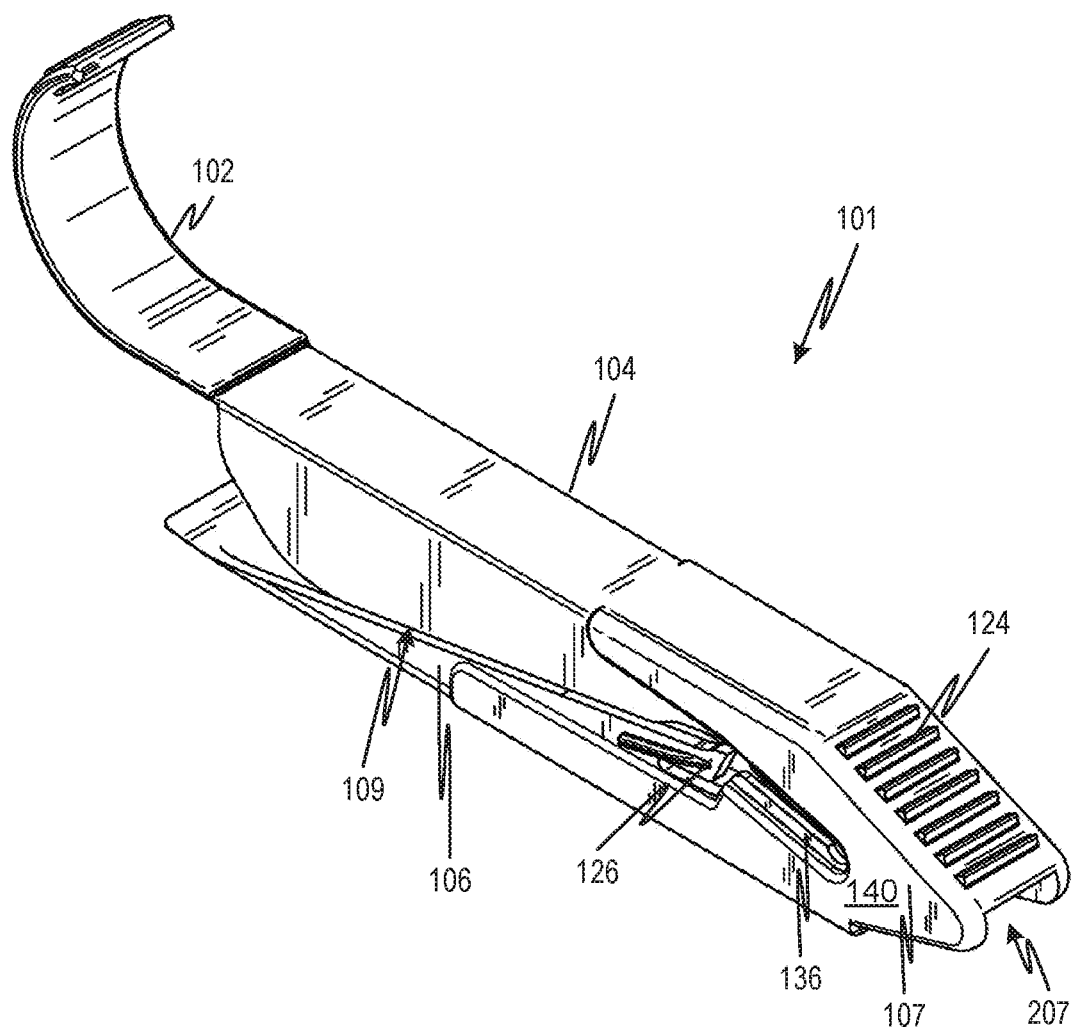
FIGS. 14A and 14B illustrate a needle guard according to embodiments of the disclosed subject matter.
Figure 14B:
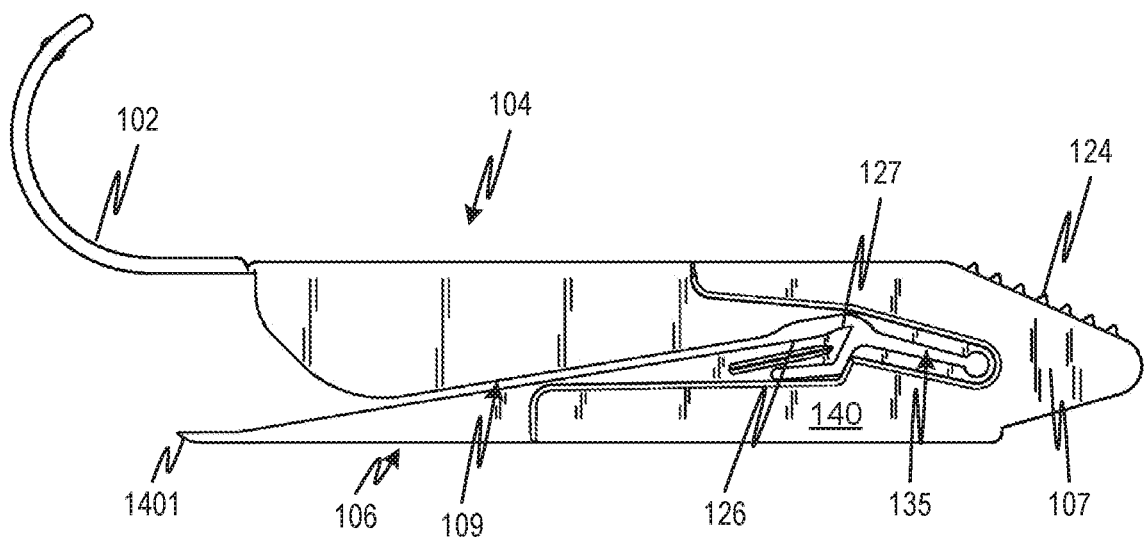

Referring to FIGS. 14A and 14B, the finger shield 102 in an embodiment has a uniform thickness. In another embodiment, the upper surface of finger shield 102 may have ribs akin to ribs 124 on hinge 107, though these ribs are not illustrated on finger shield 102 and only on hinge 107. The embodiment also has a fixed width of front slot 109 but as indicated above the embodiment may be modified to have the narrowing slot as in FIG. 7A. The present figures show specific details such as surfaces and transitions between surfaces that improve the usability of the needle guard 101. These details include the smooth flat roof 115, shape and relative size of the opening 207, and relative thickness of the thickened region 140. The drawings also show a to-scale embodiment. Note also that details of the drawing indicate aspects that are essential for molding in a three part dual action injection molding process as will be appreciated by those of skill in the art.

Figure 11A:
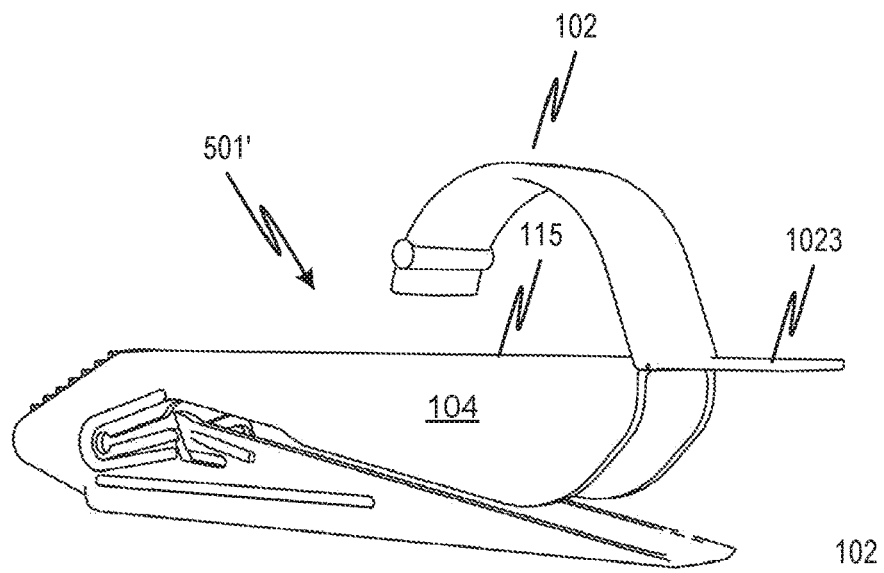
FIGS. 11A and 11B illustrate a needle guard according to embodiments of the disclosed subject matter with FIG. 11A showing the configuration after being freed from a mold and FIG. 11B showing the configuration after being put in an operating state.

Referring to FIG. 11A, in another embodiment, the finger shield 102 has a uniform thickness but may also be non-uniform as described with reference to FIGS. 5A and 5B. In an embodiment, a needle guard 501 is substantially as needle guard 101 in all respects except that as a molded piece 501' as released from the mold, the finger shield 102 and a safety flap 1023 are molded as shown in FIG. 11A. It will be confirmed by inspection that the shape of molded piece 501' permits the use of two mold halves and a core that can be drawn out of the internal space of the molded unit shown. Thus, as shown in FIG. 11A, the finger shield 102 is molded in the position shown above the roof 115 with a safety flap 1023 extending away from roof 115 in the direction from the rear of the molded piece 501' toward the front of the molded piece 501' to permit the withdrawal of a mold core in a single-shot, three-part molding operation. After molding, the finger shield 102 carrying the safety flap 1023 may be pivoted about a living hinge 1027B which is illustrated in FIG. 12, to its final position for use shown in FIG. 11B.

Figure 11B:
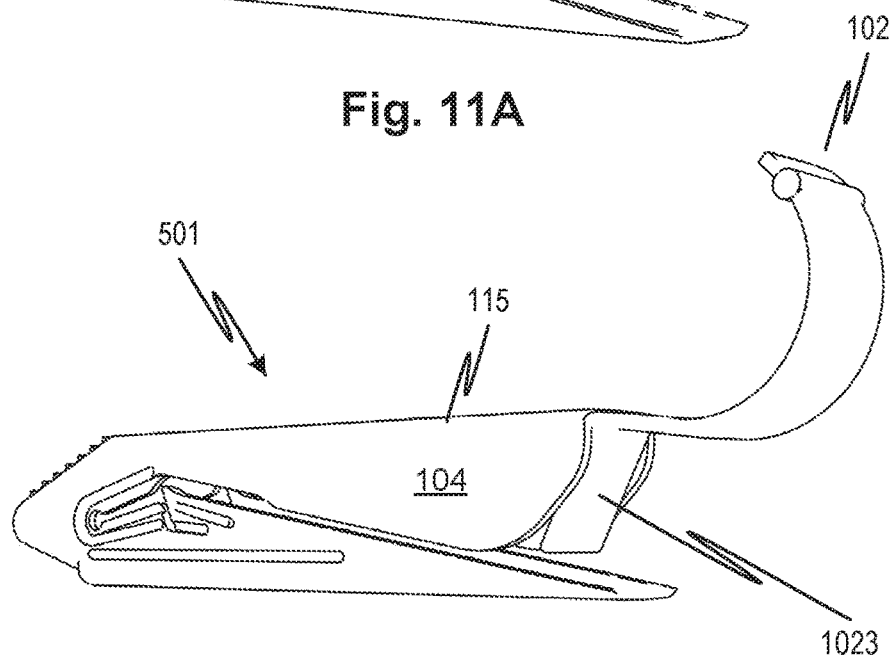
Figure 12:
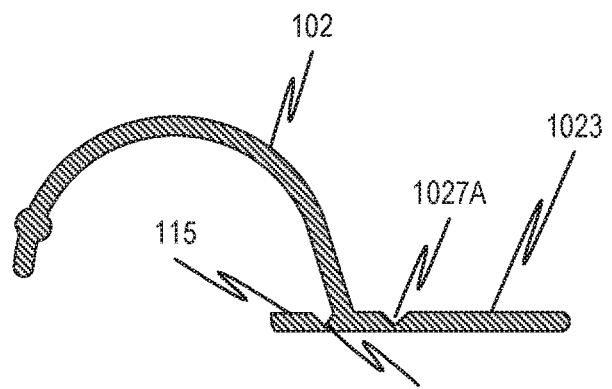
FIG. 12 illustrates a finger shield of a needle guard according to embodiments such as disclosed in FIGS. 11A and 11B.

FIG. 12 illustrates a cross sectional view of finger shield 102 with safety flap 1023 integrally connected to roof 115 of the upper jaw 104. As shown in FIG. 12, portions of material adjacent to the finger shield 102 are molded so they are thinner to form living hinges to enable the finger shield 102 to rotate into position and to allow the safety flap 1023 to flex passively when the winged needle 90 is pulled past it. Thus, when the needle guard 101 is used, the finger shield 102 is rotated down about the front end 120 of the upper jaw as shown in FIG. 11B, which also rotates safety flap 1023 into the opening of cavity 112, as shown in FIG. 11B. The safety flap 1023 may be thin enough to permit the winged needle 90 to pass by when it is drawn into the needle guard 101, and still overly an inserted needle to protect a user inserting a finger or other body part into the cavity 112, thus further reducing the possibility of an accidental puncture. Alternatively, the flexibility that permits the safety flap 1023 to permit the winged needle to pass may be provided (if the safety flap 1023 itself is thick or otherwise inflexible) or facilitated by means of a further living hinge 1027A. The safety flap 1023 may be coated with an absorbent material and/or may be made hydrophilic through a surface treatment such as electrical discharge machining. This will help prevent blood that may be in or on the cannula 52 from leaking out of the front opening of the needle guard 101. An absorbent material block can also be attached to the safety flap 1023, similar to the block 802 in FIG. 9. When the finger shield 102 is put into use, the block 802 would be on the inner side of the safety flap 1023 and in position to absorb stray blood from the cannula 52. It should be evident that the safety flap 1023 covers the tip of a cannula in the stored position after it is fully retracted and locked so even if a body part were pushed into the front end of the needle guard 501, the safety flap 1023 isolates the body part from the tip of the cannula 52.

Figure 13A:
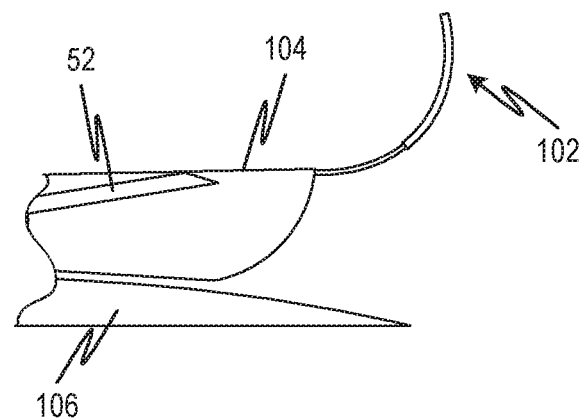
FIGS. 13A, 13B, and 13C illustrate a method of using a finger shield of a needle guard according to embodiments of the disclosed subject matter.
Figure 13B:
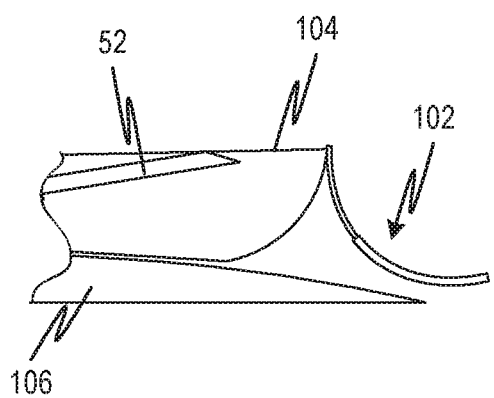
Figure 13C:
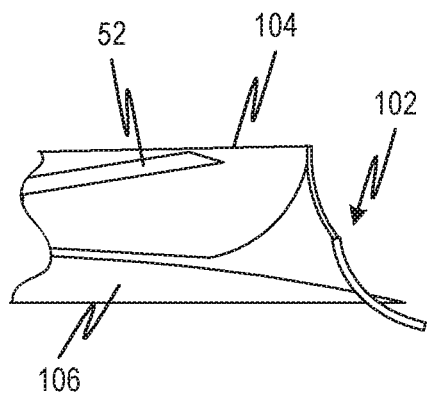

In yet another embodiment, after use, the finger shield 102 can be folded and locked in engagement with the lower jaw 106 to block cavity 112, as shown in FIGS. 13A-13C. FIG. 13A illustrates the needle guard 101 after the winged needle 90 has been fully pulled into the needle guard. The pointed end of the needle is pressed against roof 115 of the upper jaw 104. Though the needle is now safely stored, it is advantageous to further prevent a user, such as a child, from inserting a finger into the cavity 112. To this end, finger shield 102 has an opening that mates with the front end 122 of the lower jaw. FIG. 13B illustrates the finger shield 102 being bent down toward lower jaw 106, and FIG. 13C illustrates the final position where the finger shield 102 is mated to the lower jaw 106, closing off the cavity 112.

Figure 9:
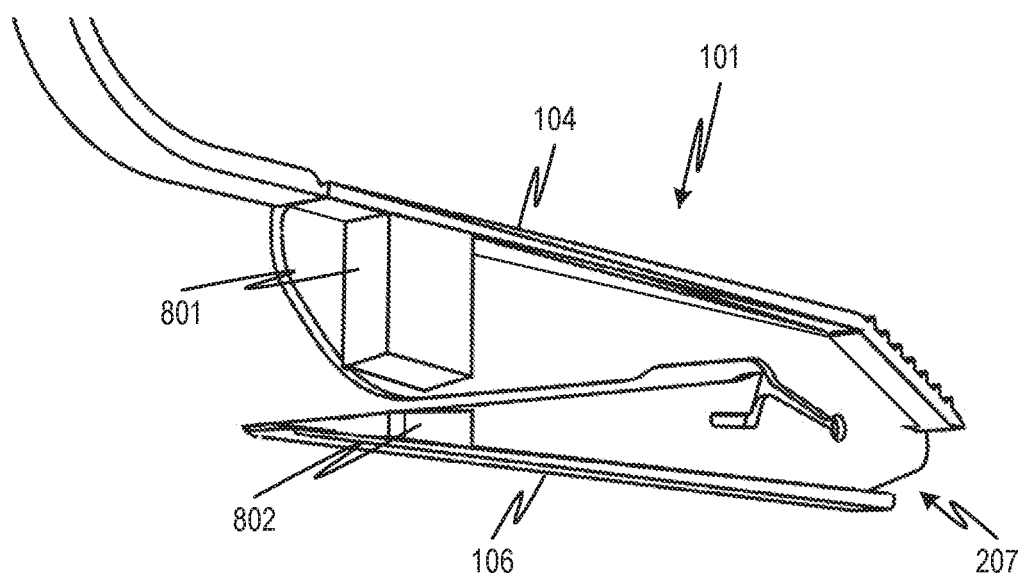
FIG. 9 illustrates a cut-away view of a needle guard with a resilient plug according an embodiment of the disclosed subject matter.

Another risk from stored cannulae is leaking blood or other bodily fluids that remain in the cannula after storage in the needle guard. A mechanism to reduce or prevent or loss of such fluid from a stored cannula provides further utility. To this end, the cavity 112 may be provided with various devices or coatings to absorb or block the flow of blood. FIG. 9 shows a cut-away view of needle guard 101 with a resilient block 801 and 802 placed inside the cavity 112. The block 801 may have two parts indicated at 801 and 802 and may be of foam or other material and may be absorbent, hydrophilic, or hydrophobic. The block parts 801 and 802 may be connected by a thin tearable sheet (not shown) to permit them to be stuffed into the front end of the needle guard 101 after molding in a single operation. Alternatively, they may be emplaced by a fixture that aligns them with respect to each other. They may be held in place by adhesive or locked by engagement features in the interior of the needle guard such as a roughened surface or pins or some other suitable mechanism. The space between the two block parts 801 and 802 allows the winged needle 90 to pass but helps to block blood or other fluid from escaping. The block parts 801 and 802 may have other suitable shapes that do not interfere with wings 50 when winged needle 90 is pulled through the needle guard. Block parts 801 and 802 may be of foam, gauze, or other material. In further embodiments, only a single block part 801 is used. Absorbent material blocks 801 and 802 can be made of a material that not only absorbs stray blood, but is firm enough to also prevent accidental needle punctures if a user presses a finger firmly into the front opening of the cavity 112 of the needle guard after the needle has been retracted to attempt to force the jaws apart through brute force.

Figure 10:
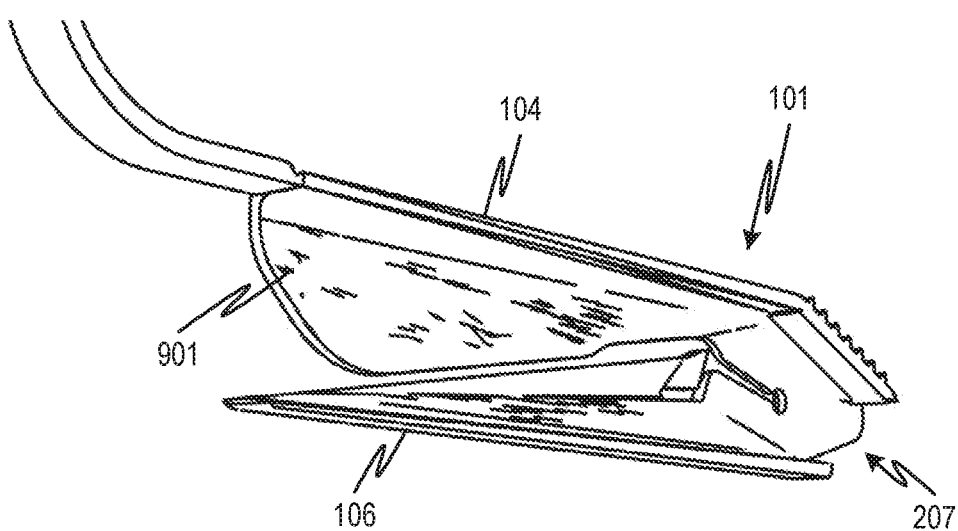
FIG. 10 illustrates a cut-away view of a needle guard with an absorbent surface according embodiments of the disclosed subject matter.

FIG. 10 shows a cut-away view of another embodiment of needle guard 101 where cavity 112 has an inner surface 901. The inner surface 901 is the inner surface of side walls 113 and 114 and the inner surface of roof 115 and floor 125. The inner surface is coated with an absorbent coating or hydrophilic surface treatment. The inner surface 901 may be textured to provide a hydrophilic surface that attracts stray blood drops and causes them to cling to the inner surface of cavity 112 rather than falling out. The embodiment of FIG. 9 will be combined with the embodiment of FIG. 10, where an absorbent coating is provided on inner surface 901 and absorbent material blocks 801 and 802 are provided in the cavity 112.

The needle guard 101 according to embodiments of the disclosed subject matter is made of high density polyethylene (HDPE) which has thermal properties that can bias the upper jaw against the lower jaw as described above. HDPE has a flexural modulus of over 300 Mpa. In embodiments, the HDPE has a flexural modulus of over 1000 Mpa. In embodiments, the HDPE has a flexural modulus of at least 1200 Mpa. The high flexural modulus of HDPE increases the needle guard's resistance to twisting. HDPE use also facilitates sterilization because it is compatible with gamma irradiation sterilization. HDPE also provides a low coefficient of friction between the wings and the needle guard, making it easy to withdraw the needle into the needle guard with a smooth and continuous motion. Other suitable materials include polypropylene and low density polyethylene.

An exemplary embodiment of the disclosed subject matter includes a needle set that has a needle guard (101) and a winged needle (90). The needle guard (101) has elongate upper and lower jaws (104, 106) each defining a channel (109, 135) and joined at a hinge portion (143), each jaw having depending side walls (113, 114) with elongate edges parallel to a longitudinal axis of each channel, each edge (108, 110) of each jaw being aligned with and spaced from a respective edge of the other jaw defining elongate slots along the side walls. The winged needle has a cannula (52), a hub (49), and a pair of wings (53). A tube (60) is connected to the cannula (52) by the hub (49). The hinge (107) has an opening (207) into which the tube (60) is received. The side walls (113, 114) are spaced apart to permit the hub (49) to be received between the jaws (104, 106) with the wings (50, 51, 53) in the slots (109, 135). Each elongate slot has an open end opposite the hinge portion and the elongate slots progressively narrow to a first spacing that is narrower than a thickness of each wing portion (51) at a point thereof that is aligned with a respective pair of the edges, and thereafter expands linearly to a second spacing that is substantially equal to the thickness of each wing portion (51).

In an embodiment, the side walls (113, 114) are thicker at the hinge portion (143) than at the open end.

In an embodiment, a cross-section of a cylindrical space between the jaws (104, 106) and in a plane perpendicular to the longitudinal axis is constant along a majority of a length of the needle guard, except for a vertical dimension thereof that diminishes progressively from a maximum dimension at the hinge portion (143) to a minimum dimension at the open end (120, 122), the maximum and minimum dimensions differing by the difference between the first and second spacings.

In an embodiment, a cross-section of a cylindrical space between the jaws (104, 106) and perpendicular to said longitudinal axis is uniform in a horizontal direction and progresses, in the vertical direction, from a maximum dimension at the hinge portion to a minimum dimension at the open end, the maximum and minimum dimensions differing by the difference between the first and second spacings. In an embodiment the first spacing may be zero.

In an embodiment, the jaws (104, 106) define a space therebetween that has a negative draft. The negative draft allows a center mold piece to be removed from the space between the jaws after the needle guard 101 is manufactured. In an embodiment the magnitude of the negative draft is equal to the difference between the first and second spacings.

In an embodiment the channels defined by the jaws (104, 106) have C-shaped cross-sections.

In an embodiment of the disclosure, a method of guarding a needle includes drawing a winged needle (90) into a cylindrical guard (101) having sidewalls (113, 114) with elongate slots (109, 135) therein, the drawing including forcing a respective wing (50, 51, 53) of said winged needle into a respective one of the slots. The drawing progressively forces the elongate slots open to a width equal to a thickness of the wings (50, 51, 53) against an urging force generated by a hinge portion (143) of the channel. During the drawing, a non-parallel orientation of the axes of the winged needle and the cylindrical guard is prevented by interferingly engaging the wings (50, 51, 53) with edges of the elongate slots during the drawing.

In an embodiment the forcing includes prying the cylindrical guard apart by urging the wings (50, 51, 53) into progressively narrowing entrances of the elongate slots (109).

In an embodiment the interferingly engaging includes interferingly engaging steps in the surface of the wings (50, 51, 53) with the edges (134, 136).

In an embodiment, the method may include positioning a lower portion (106) of the cylindrical guard underneath the winged needle (90) prior to said drawing.

In an embodiment, the preventing may include, prior to the forcing, guiding a central hub (49) of the winged needle (90) between barriers (114) on either side of said lower portion.

In an embodiment, the drawing may include drawing the wings (50, 51, 53) into expanded slot segments (138) of the elongate slots (109, 135) where the width of the slots expands and thereafter, proceeding further, bends where an edge of each slot defines a deflectable portion (126), the drawing further causing the wings to be urged against the deflectable portion as both the deflectable portion and the wings deform, the expanded slot segments being sized such that tail ends of the wings move across the expanded slot segments without friction in an initial stage of passing the deflectable portion.

In an embodiment, the drawing may include drawing the wings (50, 51, 53) into expanded slot segments (138) of the elongate slots (109, 135) where the width of the slots expands and thereafter, proceeding further, bends where an edge of each slot defines a deflectable portion (126), the deflectable portion having hook shapes (127) over which a leading edge of the wings rides after it enters the expanded slot segments, drawing further causing the wings to be urged against the deflectable portion as both the deflectable portion and the wings deform in order to follow the elongate slots through the bends.

In an embodiment, a needle set includes a needle guard (101), a winged needle (90) with a cannula (52) that has a hub (49) with a pair of wings (50, 51, 53), and a tube (60) connected to the cannula by the hub. The needle guard has elongate upper and lower jaws (104, 106) each defining a channel and joined at a hinge portion (143), each jaw having depending side walls with elongate edges parallel to a longitudinal axis of each channel, each edge of each jaw being aligned with and spaced from a respective edge of the other jaw defining elongate slots (109, 135) along the side walls. The hinge has an opening 207 into which the tube (60) is received and the side walls are spaced apart to permit the hub (49) to be received between the jaws (104, 106) with the wings (50, 51, 53) in the slots (109, 135). The lower jaw (106) extends beyond the upper jaw (104).

In an embodiment, the lower jaw (106) is C-shaped at its distal end defining sloping barriers on each side thereof to permit the lower to jaw (106) to be positioned beneath the hub (49) while the cannula (52) is inserted in a patient.

In an embodiment, the hub (49) has a protrusion or a raised nub (54) that fits between the barriers when the lower jaw is positioned beneath the hub.

In an embodiment, the lower jaw (106) has a rounded front edge.

In an embodiment, the lower jaw has a rounded surface it its front edge (122) having a center of curvature that runs parallel to a front edge thereof.

In an embodiment, a method of guarding a needle includes drawing a winged needle into a cylindrical guard having sidewalls with elongate slots therein, the drawing including guiding a respective wing of the winged needle into a respective one of the slots. Prior to the drawing, the method includes positioning a lower portion of cylindrical guard between a hub of the winged needle and the skin of a patient to at least partially support and guide the hub as it is drawn. During said drawing, the method also includes preventing a non-parallel orientation of the axes of the winged needle and the cylindrical guard by interferingly engaging the wings or a hub of the winged needle with edges defining the elongate slots during said drawing.

In an embodiment, the drawing includes forcing effective to pry the cylindrical guard apart by urging the wings into progressively narrowing entrances of the elongate slots until the wings hold the slots open and the wings can slide therethrough.

In an embodiment, the interferingly engaging includes interferingly engaging steps in the surface of the wings with the edges.

In an embodiment, the preventing includes, prior to said forcing, guiding a central hub of the winged needle between barriers on either side of said lower portion.

In an embodiment, the drawing further includes drawing the wings into expanded slot segments of said elongate slots where the width of the slots expands and thereafter, proceeding further, bends where an edge of each slot defines a deflectable portion, the drawing further causing the wings to be urged against the deflectable portion as both the deflectable portion and the wings deform, the expanded slot segments being sized such that tail ends of the wings move across the expanded slot segments without friction in an initial stage of passing the deflectable portion.

In an embodiment, the drawing further includes drawing the wings into expanded slot segments of the elongate slots where the width of the slots expands and thereafter, proceeding further, bends where an edge of each slot defines a deflectable portion, the deflectable portion having hook shapes or barbs over which a leading edge of the wings rides after it enters said expanded slot segments, drawing further causing the wings to be urged against the deflectable portion as both the deflectable portion and the wings deform in order to follow the elongate slots through the bends.

In an embodiment, a needle set includes a winged needle (90) and a channel member (104, 106) having a longitudinal axis. The winged needle includes a hub (49), a cannula (52), and wings (50, 51, 53). The channel further has sidewalls (113, 114) with slots opposite each other and parallel to said axis. The slots are open at an open end of the channel member and closed at a hinge end of the channel member. Each slot has a first portion (109) beginning at the open end where it has a constant width or a width that increases linearly from the open end toward the hinge end. Each slot has a progressively narrowing entry at the open end leading to the first portion (109). Each slot has a transition portion (138) at an end thereof near the hinge end (143) with a width greater than a maximum width of the first portion, the transition having a length that is a minor fraction of the first portion. Each slot has a narrow terminal portion that forms an angle with the first portion and transition portion such that there is a bend in each slot with the terminal portion on one side and the transition and first portions on the other side. The transition portion (138) having, along one edge thereof, a latch (126) with a concave niche formed by a corner in said one edge.

Another embodiment includes a needle guard (101) for protecting a user from a needle (90) pulled from a front end of the needle guard to a rear end of the needle guard. The needle guard includes an upper jaw (104), a hinge (107), and a lower jaw (106). The upper jaw includes a roof (115), two opposed upper side walls (113) extending down from the roof, where each upper side wall includes an upper edge integral with the roof, a curved side edge at the front end, and a substantially straight bottom edge (108) abutting a bridge slot (138) at a rear end of the bottom edge. The upper jaw abuts the hinge (107), which in turn abuts the lower jaw (106). The hinge includes an upper hinge edge (134) and a lower hinge edge (136) defining a rear slot (135). The lower jaw abuts the hinge and includes a floor (125), two opposed lower side walls (114) extending up from the floor toward the upper jaw. Each lower side wall includes a bottom edge integral with the floor, a top edge (110) facing the bottom edge (108) of the upper side wall and extending toward the front end to meet the bottom edge of the lower side wall. The top edge of the lower side wall and the bottom edge of the upper side wall define a front slot (109). A latch (126) extends from the lower side wall opposite the bridge slot, wherein the front slot defines a cavity (112) opening at the front end of the needle guard, the front slot (109) connects to the rear slot (135), and the latch (126) bends down in response to a winged needle (90) passing through the front slot (109) and the bridge slot (138). The latch (126) rises to block the winged needle (90) from pulling out of the rear slot once the winged needle passes beyond the latch.

In another exemplary embodiment disclosed above, the upper side wall (113), the lower side wall (114), and the hinge (107) include a thickened region (140) that has wall thickness greater than the wall thickness at other regions of the needle guard.

In another exemplary embodiment disclosed above, the thickened region of the upper side wall abuts the hinge.

In another exemplary embodiment disclosed above, the thickened region of the lower side wall abuts the hinge.

In another exemplary embodiment disclosed above, the thickened region of the hinge abuts the upper jaw and the lower jaw.

In another exemplary embodiment disclosed above, the roof is flat or has a triangular cross-section, like a gable roof of a house.

In another exemplary embodiment disclosed above, the upper edge of the upper side wall is substantially straight.

In another exemplary embodiment disclosed above, the floor is substantially flat.

In another exemplary embodiment disclosed above, the lower jaw extends in the front beyond the upper jaw.

In another exemplary embodiment disclosed above, the floor includes a front edge (122) that has a rounded shape.

In another exemplary embodiment disclosed above, a finger shield (102) extends from a front end of the roof of the upper jaw, the finger shield including a curved strip extending up from the front end of the roof.

In another exemplary embodiment disclosed above, the finger shield (102) includes a thin portion (1022) immediately abutting the roof of the upper jaw, and a thick portion (1021) having a thickness greater than the thickness of the thin portion abutting the thin portion.

In another exemplary embodiment disclosed above, the width of the finger shield (102) measured perpendicularly to the upper side wall is substantially same as the width of the roof (115) of the upper jaw.

In another exemplary embodiment disclosed above, the finger shield (102) is configured to fold toward the lower jaw after the winged needle is pulled into the needle guard, to engage the lower jaw to close the front end of the needle guard.

In another exemplary embodiment disclosed above, finger shield (102) also includes a safety flap (1023) extending from the roof toward the floor when the finger shield is pressed toward the lower jaw.

In another exemplary embodiment disclosed above, the rear slot (135) of the hinge is bounded by a region of material having a first thickness that is smaller than the thickness of the thickened region of the hinge. The region of the material having the first thickness cools faster than the thickened region of the hinge when the needle guard is molded or cast. The difference in cooling time pulls the upper jaw (104) toward the lower jaw (106). This may result in a positive draft of the needle guard 101 even when the mold or cast has a negative draft.

In another exemplary embodiment disclosed above, the upper jaw (104) is biased against the lower jaw (106) by the hinge (107), and the top edge (110) of the lower side wall is in contact with the bottom edge (108) of the upper side wall at least at the front end of the needle guard.

In another exemplary embodiment disclosed above, the top edge (110) of the lower side wall is parallel to the bottom edge (108) of the upper side wall.

In another exemplary embodiment disclosed above, the front slot (109) tapers from the front end of the needle guard toward the rear end of the needle guard.

In another exemplary embodiment disclosed above, the latch (126) includes a barb (127) protruding from latch toward the bridge slot. The barb (127) forms a kind or a hockey-stick shape on the upper edge of the latch (126).

In another exemplary embodiment disclosed above, the winged needle (90) strums the latch when the winged needle passes over and clears the barb (127), producing an audible and palpable click.

In another exemplary embodiment disclosed above, a safety needle set includes a winged needle (90) having a hub (49) with wings (50, 51, 53) extending in opposite directions, a cannula (52) held in the center of the hub, and a tube (60) extending from the hub on a side opposite the needle. The safety needle set also includes a needle guard (101) according to any combination of the exemplary embodiments disclosed above.

As used herein, the term "cylinder" or "cylindrical" may refer to a hollow structure and is not limited to a structure with a circular cross-section. For example, a hollow elongate prism or one elongate structure with an elliptical cross-section or piece-wise closed cross-section may be identified by the term "cylinder." Note that any of the embodiments may be modified by providing additional openings, for example the floor of the needle guards 101 may be opened (U-shaped) to permit a snap-on type of arrangement that allows the user to emplace the needle guard over a winged needle and tube set.

Features of the disclosed embodiments may be combined, rearranged, omitted, etc., within the scope of the disclosed subject matter to produce additional embodiments. Furthermore, certain features may sometimes be used to advantage without a corresponding use of other features. It is, thus, apparent that there is provided, in accordance with the present disclosure, a needle guard and associated manufactures, components, systems, and methods of use. Many alternatives, modifications, and variations are enabled by the present disclosure. While specific embodiments have been shown and described in detail to illustrate the application of the principles of the disclosure, it will be understood that the disclosed subject matter may be embodied otherwise without departing from such principles. Accordingly, Applicants intend to embrace all such alternatives, modifications, equivalents, and variations that are within the spirit and scope of the present disclosure.

The invention claimed is:

1. A needle set, comprising:
a needle guard having an upper jaw and a lower jaw, the upper jaw and the lower jaw each defining a channel and being joined at a hinge, the upper jaw having upper side walls parallel to a longitudinal axis of the needle guard, the lower jaw having lower side walls parallel to the longitudinal axis, edges of the upper jaw being aligned with and spaced from respective edges of the lower jaw and defining slots between the upper side walls and the lower side walls, the upper jaw, the upper side walls, the lower jaw, and the lower side walls defining a boundary of a volume inside the needle guard, the volume having a rectangular cross-section shape taken perpendicular to the longitudinal axis;
a winged needle having a cannula and a hub with a pair of wings;
a tube connected to the cannula by the hub;
the hinge having an opening into which the tube is received;
the upper side walls and the lower side walls being laterally spaced apart to permit the hub to be received between the upper jaw and the lower jaw with the wings in the slots;
each slot of the slots having an open end opposite the hinge, the slots progressively narrowing to a first spacing that is narrower than a thickness of each wing of the wings at a point on each wing that will be aligned with a respective pair of said edges when the wings are retracted into the needle guard, and thereafter expanding progressively to a second spacing that is substantially equal to said thickness of each wing, wherein
a height of a first cross-section of the volume inside the needle guard in a plane perpendicular to said longitudinal axis and taken at a first point, at the open end of each slot, is smaller than a height of a second cross-section of the volume inside the needle guard in a plane perpendicular to said longitudinal axis and taken at a second point, adjacent to the hinge of the needle guard, and
the height of the first cross-section at the first point and the height of the second cross-section at the second point differing by a difference between said first and second spacings.

2. The set of claim 1, wherein the upper side walls and the lower side walls are thicker at said hinge than at said open end of each slot.

3. The set of claim 1, wherein said first spacing is zero.

4. The set of claim 1, wherein the volume inside the needle guard has a negative draft.

5. The set of claim 4, wherein a magnitude of the negative draft is equal to the difference between said first and second spacings.

6. The set of claim 1, wherein the channel defined by each of the upper jaw and the lower jaw has a C-shaped cross-section.

7. The set of claim 1, wherein the lower jaw has a floor that is substantially flat.

8. The set of claim 7, wherein the floor includes a front edge that has a rounded shape.

9. A needle guard for protecting a user from a winged needle pulled from a front end of the needle guard to a rear end of the needle guard, the needle guard comprising:
an upper jaw that includes
a roof,
two opposed upper side walls extending down from the roof, each upper side wall of the two opposed upper side walls including
an upper edge depending from the roof,
a curved side edge at the front end, and
a substantially straight bottom edge abutting a bridge slot at a rear end of the bottom edge, the upper jaw abutting a hinge;
the hinge abutting the bridge slots of the upper jaw and a lower jaw, the hinge including an upper hinge edge and a lower hinge edge defining a rear slot; and the lower jaw abutting the hinge and including
  a floor,
  two opposed lower side walls extending up from the floor toward the upper jaw, each respective one lower side wall of the two opposed lower side walls including
    a bottom edge depending from the floor,
    a top edge facing the bottom edge of one of the two opposed upper side walls and extending toward the front end to meet the bottom edge of the respective one lower side wall, said top edge of the respective one lower side wall and said bottom edge of the one of the two opposed upper side walls defining a front slot, and
  a latch extending from the respective one lower side wall opposite the bridge slot of one of the two opposed upper side walls,
  the bridge slot being a slot portion that is distinct from the front and rear slots with a vertical slot width that is greater than a vertical slot width of the front slot and greater than a vertical slot width of the rear slot to facilitate movement of the winged needle from the front slot to the rear slot, wherein
the front slot defines a cavity opening at the front end of the needle guard,
the front slot connects to the rear slot,
the latch bends down in response to the winged needle passing through the front slot and the bridge slot and rises to block the winged needle from pulling out of the rear slot, and
on each respective side of the needle guard, the bridge slot projects beyond a point where an extension of the substantially straight bottom edge of a respective upper side wall of the two opposed upper side walls would intersect an extension of the upper hinge edge.

10. The needle guard according to claim 9, wherein each upper side wall of the two opposed upper side walls, each lower side wall of the two opposed lower side walls, and the hinge include a thickened region that has a first wall thickness that is greater than a second wall thickness at other regions of the needle guard.

11. The needle guard according to claim 10, wherein the rear slot of the hinge is bounded by a region of a material having a third thickness that is smaller than the first wall thickness of the thickened region of the hinge.

12. The needle guard according to claim 11, wherein the region of the material having the third, smaller wall thickness cools faster than the thickened region of the hinge when the needle guard is molded or cast.

13. The needle guard according to claim 9, wherein the roof is flat.

14. The needle guard according to claim 9, wherein the upper edge of each upper side wall of the two opposed upper side walls is substantially straight.

15. The needle guard according to claim 9, wherein the floor is substantially flat.

16. The needle guard according to claim 9, wherein the lower jaw extends in the front beyond the upper jaw.

17. The needle guard according to claim 16, wherein the floor includes a front edge that has a rounded shape.

18. The needle guard according to claim 9, further comprising:
  a finger shield extending from a front end of the roof of the upper jaw, the finger shield including a curved strip extending up from the front end of the roof, wherein the finger shield includes a thin portion immediately abutting the roof of the upper jaw, and
  a thick portion, having a thickness greater than a thickness of the thin portion, abutting the thin portion.

* * * * *